US007183457B2

(12) United States Patent
Rafalski et al.

(10) Patent No.: US 7,183,457 B2

(45) Date of Patent: Feb. 27, 2007

(54) PLANT DISEASE RESISTANCE GENES

(75) Inventors: J. Antoni Rafalski, Wilmington, DE (US); Guo-Hua Miao, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/013,592

(22) Filed: Dec. 15, 2004

(65) Prior Publication Data

US 2006/0037097 A1 Feb. 16, 2006

Related U.S. Application Data

(62) Division of application No. 09/857,896, filed on Jun. 11, 2001, now Pat. No. 6,846,972.

(51) Int. Cl.

| | |
|---|---|
| ***A01H 1/00*** | (2006.01) |
| ***C07H 21/04*** | (2006.01) |
| ***C07K 14/415*** | (2006.01) |
| ***C12N 5/14*** | (2006.01) |
| ***C12N 9/00*** | (2006.01) |

(52) U.S. Cl. .......................... 800/295; 435/6; 435/69.1; 435/468; 435/419; 435/252.3; 435/320.1; 435/183; 530/370; 536/23.6; 800/278

(58) Field of Classification Search .................... 435/6, 435/69.1, 468, 419, 252.3, 320.1, 183; 530/370; 536/23.6; 800/278, 296

See application file for complete search history.

(56) References Cited

FOREIGN PATENT DOCUMENTS

WO WO 98/04586 A2 2/1998
WO WO 00/01722 A1 1/2000

OTHER PUBLICATIONS

Kaneko et al., DNA Research, Apr. 30, 1998, vol. 5, No. 2, pp. 131-145.*

Rainer Buschges et al., Cell, vol. 88:695-705, 1997, The barley Mio gene: A novel control element of plant pathogen resitance.

Kim E. Hammond-Kosack et al., Annu. Rev. Plant Phys. Plant Mol. Biol., vol. 48:575-607, 1997, Plant Disease Resistance Genes.

H. H. Flor, Annu. Rev. Phytopathol., vol. 9:275-296, 1971, Current status of the gene-for-gene concept.

Guo-Liang Wang et al., Mol. Plant Microbe Interact., vol. 9(9):850-855, 1996, The cloned gene, Xa21, confers resistance to multiple *Xanthomonas oryzae* pv. oryzae isloates in transgenic plants.

National Center for Biotechnology Information General Identifier No. 1877221, Mar. 7, 1997, Bueschges, R. et al., The barley Mio gene: A novel control element of plant pathogen resistance.

National Center for Biotechnology Information General Identifier No. 2459447, Oct. 8, 1997, Rounsley, S.D. et al., *Arabdiopsis thaliana* chromosome II BAC F4P9 genomic sequence.

National Center for Biotechnology Information General Identifier No. 3212880, Apr. 5, 2000, Lin, X. et al., Sequence and analysis of chromosome 2 of the plant *Arabidopsis thaliana.*

Xiaoying Lin et al., Nature, vol. 402:761-768, 1999, Sequence and analysis of chromosome 2 of the plant *Arabidopsis thaliana.*

National Center for Biotechnology Information General Identifier No. 2765817, Jan. 8, 1998, Panstruga, R.

National Center for Biotechnology Information General Identifier No. 5051767, Aug. 27, 1999, Bevan, M. et al.

National Center for Biotechnology Information General Identifier No. 4585879, Apr. 16, 1999, Federspiel, N.A. et al.

National Center for Biotechnology Information General Indentifier No. 2765821, Jan. 8, 1998, Panstruga, R.

* cited by examiner

*Primary Examiner*—Phuong T. Bui

(57) ABSTRACT

This invention relates to an isolated nucleic acid fragment encoding an Mlo homolog. The invention also relates to the construction of a chimeric gene encoding all or a portion of the Mlo homolog, in sense or antisense orientation, wherein expression of the chimeric gene results in production of altered levels of the Mlo homolog in a transformed host cell.

11 Claims, 6 Drawing Sheets

```
SEQ ID NO:41  M-----------------GHGGE------GMSLEFTPTWVVAGVCTVIVAISLAVERLLH
SEQ ID NO:40  MITRSRCRRSLLWFLVFHGGATATGAPSGGKELSQTPTWAVAVVCTFLILISHLLEKGLQ
SEQ ID NO:39  M--------------------SDKKG-VPARELPETPSWAVAVVFAAMVLVSVLMEHGLH
SEQ ID NO:42  M--------------------ADQ---VKEKTLEETSTWAVAVVCFVLLLISIVIEKLIH
SEQ ID NO:08  M-----------------SGGGEE-----GATLEFTPTWVVAAFCTVIVAISLAAERLLH
SEQ ID NO:12  M--------------------AAGESSSSSRDLDQTPTWAVAAVCTVFILVSIALEKSLH
SEQ ID NO:14  M-----------------GGGGEE-----GNNLEFTPTWVVAVVCSVIVAASFAAERFLH
SEQ ID NO:28  M--------------------GG-------KTLQETPTWAVAVVCFVLLSISILIEHILH
SEQ ID NO:32  M--------------------AEDYEYPPARTLPETPSWAVALVFAVMIIVSVLLEHALH
SEQ ID NO:38  M-----------------AGGGGK-----AKPLEYTPTWIVALVCSVMIIISLLFERLLH
              1                                                          60

SEQ ID NO:41  YFGTVLKKKKQKPLYEALQKVKEELMLLGFISLLLTVFQGL-ISKFCVKENVLMHMLPCS
SEQ ID NO:40  RLANWLWKKHKNSLLEALEKIKAELMILGFISLLLTFGE-PYILKICVPRKAALSMLPCL
SEQ ID NO:39  KLGHWFQHRHKKALWEALEKMKAELMLVGFISLLLIVTQDPIIAKICISEDAADVMWPCK
SEQ ID NO:42  KIGSWFKKKNKKALYEALEKVKAELMLMGFISLLLTIGQG-YISNICIPKNIAASMHPCS
SEQ ID NO:08  YGGKFLKAKDQKPLYEALQKIKEELMLLGFISLLLTVTQNG-ITKICVRPSLTLHMLPCN
SEQ ID NO:12  KVGTWLGQKKKKALLEALEKVKAELMILGFISLLLTFGQ-SYIVRICIPEKLADNMLPCP
SEQ ID NO:14  YGGKFLKRKNQKPLYEALEKIKEELMLLGFISLLLTITQNG-IIRICVPVGWTHHMLPCS
SEQ ID NO:28  LIGKWLKKKHKRALCEALEKIKSELMLLGFISLLLTVGQG-LISRICISEKVAGTFHPCP
SEQ ID NO:32  KLGHWFHKRHKNALAEALEKIKAELMLVGFISLLLAVTQDPISG-ICISEKAASIMRPCS
SEQ ID NO:38  RLGKRLIRSRKKPLYEALLKVKEELMLLGFISLLLTVFQGP-MGKVCVSPSAMLHLQPCK
              61                                                        120
```

FIG. 1A

```
SEQ ID NO:41  LDSR-----REAGASEHKNVTAKEHFQTFLPIVG-TTRRLLAEH-----AAVQVGYCSEK
SEQ ID NO:40  --------------SEDTVLFQKLAPSSL-------SRHLLAAGDTSIN-------C-KQ
SEQ ID NO:39  RGTEGRK---------------PSKYVDY---------------------------CPE-
SEQ ID NO:42  ASEEARKYGKKDVPKEDEEENLRRKLLQLVDS--LIPRRSLATKGYD-K-------CAEK
SEQ ID NO:08  LHD---------APANHES-----HFQTFFP--G-TARRLLSGEHSTPESASKIGYCSRK
SEQ ID NO:12  Y-----KY-KEDKKASDSEEEHRRKLLSY-------ERRYLAADTTSFK-------CSRE
SEQ ID NO:14  L-----------------------------------------------------------
SEQ ID NO:28  -----KKYYKKKEESEHRTNNGRRLLAAFLDSDNQNHRRILAAGGGD-N-------CPP-
SEQ ID NO:32  LPPGSVK----------------SKYKDYY--------------------------CAKK
SEQ ID NO:38  -----------PPPHETDHLGD----AVFTGVLG-GARRLLAGGASSSDK-----YCLKK
             121                                                        180

SEQ ID NO:41  GKVPLLSLEALHHLHIFIFVLAISHVTFCVLTVIFGSTRIHQWKKWEDSIADEKFDPETA
SEQ ID NO:40  GSEPLITLKGLHQLHILLFFLAIFHIVYSLITMMLSRLKIRGWKKWEQETLSNDYEFSID
SEQ ID NO:39  GKVALMSTGSLHQLHVFIFVLAVFHVTYSVITIALSRLKMRTWKKWETETTSLEYQFAND
SEQ ID NO:42  GKVAFVSAYGMHQLHIFIFVLAVCHVIYCIVTYALGKTKMRRWKKWEEETKTIEYQYSHD
SEQ ID NO:08  HKVPLLSVEALHHLHIFIFVLAVVHVSFSVLTVVFGGARIRQWKHWEDSIAKQNYETDRV
SEQ ID NO:12  GHEPLLSVNGLHQLHILRILLAVIHVLYSAITMMLGRLKILGWKAWEAGLQLHNYEFANA
SEQ ID NO:14  ------------------------------------------------------------
SEQ ID NO:28  GKVPFVSSEGIHQLHIFIFVLAVFHVLYCILTLALGRAKMRRWKRWEEETKTAQYQFSHD
SEQ ID NO:32  GKVSLMSTGSLHQLHIFIFVLAVFHVTYSVIIMALSRLKMRTWKKWETETASLEYQFAND
SEQ ID NO:38  DKVPLLSSDAIHQLHIFIFVLAVTHFLLSAITVLLGMAQTRNWRHWETKIQENNGSAPQM
             181                                                        240
```

FIG. 1B

```
SEQ ID NO:41  LRKRRVTHVHNHAFIKEHFLGIGKDSVILGWTQSFLKQFYDSVTKSDYVTLRLGFIMTH-
SEQ ID NO:40  HSRLRLTH--ETSFVREHT-SFWTTTPFFFYVGCFFRQFFVSVERTDYLTLRHGFISAHL
SEQ ID NO:39  PARFRFTH--QTSFVKRHL-GLSSTPGIR-WVVAFFRQFFRSVTKVDYLTLRAGFINAHL
SEQ ID NO:42  PERFRFAR--DTSFGRRHL-SFWSKSTITLWIVCFFRQFFRSVTKVDYLTLRHGFIMAHL
SEQ ID NO:08  L-KPKVTQVHQHDFIRGRFAGFGKDSAIVGWLLSFLKQFYGSVTKSDYVTLRHGFIMTH-
SEQ ID NO:12  ASKIKLIM--ETSFVRSPI-QFLIRIPIFFYIRCFFRQFYRSVNRTDYLTLRNGFITVHL
SEQ ID NO:14  ------------------------------------------------------------
SEQ ID NO:28  PERFRFAR--ETSFGRRHL-SFWAQNPVLLWIVCFFRQFVRSVPKVDYLTLRHGFMMAHL
SEQ ID NO:32  PARFRFTH--QTSFVKRHL-GLSSTPGIR-WVVAFFRQFFRSVTKVDYLTLRAGFINAHL
SEQ ID NO:38  IK-----HVQEFKFIQDHFKGHRKRSRIFGWMRSFFKQLYGSVTEEDYTTMRLGFIMKH-
             241                                                        300

SEQ ID NO:41  -CKGNPKLNFHKYMMRALEDDFKQVVGISWYLWIFVVIFLLLNVNGWHTYFWIAFIPFAL
SEQ ID NO:40  APGR--KFNFQRYIKRSLEDDFKLVVGISPVLWASFVIFLLFNVNGWRTLFWASIPPLLI
SEQ ID NO:39  SQNS--KFDFHKYIKRSMEDDFKVVYGISLPLWGVAILTLFLDINGVGTLIWISFIPLVI
SEQ ID NO:42  APGSDARFDFRKYIQRSLEEDFKTIVEINPVIWFIAVLFLLTNTNGLNSYLWLPFIPFIV
SEQ ID NO:08  -CRTNPKFNFHKYMIRALEDDFKQVVGISWDLWLFVVIFLLLNINGWHTYFWIAFIPVIL
SEQ ID NO:12  APGS--KFNFPKYIKRSLEDDFKVVVGVSPILWASVVVYLLINVNGWHTVLWAALIPVVI
SEQ ID NO:14  ------------------------------------------------------------
SEQ ID NO:28  GPHSHPKFDFRQYIKRSLEEDFKVVVEIR-------------------------------
SEQ ID NO:32  SHNS--KFDFHKYIKRSMEDDFKVVVGISLPLWCVAILTLFLDIDGIGTLTWISFIPLVI
SEQ ID NO:38  -CKGTPKFNFYSYMIRALEVDFKKVVGISWYLWAMLMIFLLLNVEGWYVYIWITLVPFIM
             301                                                        360
```

FIG. 1C

```
SEQ ID NO:41  LLAVGTKLEHVIAQLAHEVAEKHVAIEGDLVVKPSDEHFWFSKPQIVLYLIHFILFQNAF
SEQ ID NO:40  ILAVGTKLQAIMATMALEIVETHAVVQGMPLVQGSDRYFWFDCPQLLLHLIHFALFQNAF
SEQ ID NO:39  LLCVGTKLEMIIMEMALEIQDRASVIKGAPVVEPSNKFFWFHRPDWVLFFIHLTLFQNAF
SEQ ID NO:42  ILIVGTKLQVIITKLGLRIQEKGDVVKGTPLVQPGDHFFWFGRPRFILFLIHLVLFTNAF
SEQ ID NO:08  LLAVGTKLEHIITQLAHEVPEKHAAIEGDLVVQPSDEHFWFHRPHVVLFLIHFILFQNAF
SEQ ID NO:12  ILAVGTKLQAILANMALEITERHAVVQGMPLVQGSDKYFWFGQPQLVLHLIHFALFQNAF
SEQ ID NO:14  ------------------------------------------------------------
SEQ ID NO:28  ------------------------------------------------------------
SEQ ID NO:32  LLCVGTKLEMIIMEMALEIQDRASVIKGAPVVEPSNKFFWFHRPDWVLFFIHLTLFQNAF
SEQ ID NO:38  LLMVGSKMEHIITELAYEVAQKHTAIRGDLVVSPSDNFFWFHRPKLVLLLIHIVLFQNAF
              361                                                       420

SEQ ID NO:41  EIAFFFWIWVTYGFDSCIMGQVRYIVPRLVIGVFIQVLCSYSTLPLYAIVSQMGSSFKKA
SEQ ID NO:40  QITHFFWIWYSFGLKSCFHKDFNLVVSKLFLCLGALILCSYITLPLYALVTQMGSHMKKA
SEQ ID NO:39  QMAHFVWTVATPGLKKCYHTQIGLSIMKVVVGLALQFLCSYMTFPLYALVTQMGSNMKRS
SEQ ID NO:42  QLAFFVWSTYEFGLKNCFHESRVDVIIRISIGLLVQILCSYVTLPLYALVTQMGSKMKPT
SEQ ID NO:08  EIAFFFWIWVTYGFDSCIMGQVRYIVPRLVIGVFIQVLCSYSTLPLYAIVTQMGTHYKRA
SEQ ID NO:12  QITYILWIWYSFGLRNCFRTDYKLAVVKVALXM-MLCLCSYITLPLYALVTQMGSRMKTA
SEQ ID NO:14  ------------------------------------------------------------
SEQ ID NO:28  ---FFA------------------------------------------------------
SEQ ID NO:32  QMAHFVWTVATPGLKKCFHMHIGLSIMKVVLGLALQFLCSYITFPLYALVTQMGSNMKRS
SEQ ID NO:38  EIAFFFWLLVTYGFKSCIMGKPAYVITRVVISVICQVLCGYSTLPLYAVVSHMGNSFKKT
              421                                                       480
```

FIG. 1D

```
SEQ ID NO:41  IFEENVQVGLVGWAQKVKQKRDLKAAA----SNGDEGSSQAGPGPDSGSGS---------
SEQ ID NO:40  VFDEQMAKALKKWHKDIKLKK--------------GKARKLPSKTLGVSESFSL------
SEQ ID NO:39  IFDEQTSKALTNWRNTAKEKKKVRDTDMLMAQMIGDATPSRGSSPMPSRGSSPVHLLHKG
SEQ ID NO:42  VFNERVATALKSWHHTA--KKNIKH-----GRTSESTTPFSSRPTTPTHGSSPIHLLRNA
SEQ ID NO:08  IFNDHLQQNIVGWAQKAKKRKGLKA----------DGNPGQGSSQESAN-----------
SEQ ID NO:12  IFDEQTNKALKKWHMAAKKKQ--------------GGAVTLGKSSARIMDGSPI------
SEQ ID NO:14  ---------------KDKKK----------------------------------------
SEQ ID NO:28  ------------------------------------------------------------
SEQ ID NO:32  IFDEQTAKALTNWRNTAKEKKKVRDTDMLMAQMIGDATPSRGTSPMPSRASSPVHLLHKG
SEQ ID NO:38  IFDENVTEGLVNWAEKA--RRGTRTPN----KITTDASSSPIDEANGGA-----------
              481                                                       540

SEQ ID NO:41  ----------------APAAGPGAGFAGIQLSRVTRNNAGDTNNEITPDHN-----N---
SEQ ID NO:40  -------------------SSSSSATTLHRSKTTGH---SSNIIYYKQEDEEDEMSD--L
SEQ ID NO:39  ---MGRSDD--------PQSAPTSPRTQQEARDMYPVVVAHPVHRLNPNDRRRSASSSAL
SEQ ID NO:42  PHKRSRSVDESFANSFSPRNSDFDSWDPESQHETAETSNSNHRSRFGEEESEKKFVSSSV
SEQ ID NO:08  --------------------------TGIQLGSIFKKATAPGDSSSAPKADGISSV.---
SEQ ID NO:12  -------------------GNSSTVHSLAPHYTVSKLLATQPAPHQQRTRIKIKIMN--M
SEQ ID NO:14  --------------------------------------------------------K---
SEQ ID NO:28  ------------------------------------------------------------
SEQ ID NO:32  ---MGRSDD--------PQSAPTSPRTMEEARDMYPVVVAHPVHRLNPADRRRSVSSSAL
SEQ ID NO:38  ----------------------------VQMT--------NTRANSSVEQGTARLI.---
              541                                                       600
```

FIG. 1E

```
SEQ ID NO:41  -----------------------------
SEQ ID NO:40  EAGAEDAIDRIQQQEMQF--------HNS
SEQ ID NO:39  E--------------ADIPSADFSFSQ-G
SEQ ID NO:42  ELPPGPGQIRTQHEISTISLRDFSFKR--
SEQ ID NO:08  -----------------------------
SEQ ID NO:12  NPMVLSCLRWRRKQQASL.----------
SEQ ID NO:14  -----------------------------
SEQ ID NO:28  -----------------------------
SEQ ID NO:32  D--------------ADIPSADFSFSQG.
SEQ ID NO:38  -----------------------------
             601                         629
```

FIG. 1F

SEQUENCE LISTING

```
<160> NUMBER OF SEQ ID NOS: 42

<210> SEQ ID NO 1
<211> LENGTH: 1600
<212> TYPE: DNA
<213> ORGANISM: Oryza sativa

<400> SEQUENCE: 1

cttacagata agttgtgcat aaacgaatgg aaatagcagc agttacaatt taggatgttt      60

cattcccaca gaaaaagtgc aagcactttc ttgatgtaat ttcctacaga ttgcagattg     120

gaagttgtct ctgactgtgc cattatgctc ttcaatgttc atggatggca taacttgttc     180

tggttctcta caatccccct tgtagtaact ttagcagttg gaacaaagct gcaggctata     240

attgcaatga tggctgttga aattaaagag aggcatacag taattcaagg aatgccggtg     300

gtgaaactca gtgatgaaca tttttggttc gggaagccac gtctggttct tcatcttatc     360

catttcgcgt catttcaggt aacttgaaca taaagcttgc ggaaaagctt ttgcgtaaaa     420

tgcacaacct tgactcactt acatccacca aatgatgaat gtcatgcacc atagacatct     480
```

-continued

```
ggatagcagt gtcaaattga attttcacta tcatgattgc taaggaaata aagtatcagt    540

gtttagagaa tactttgttg ccacggaata cttaatctct agtctttagc atgcacttac    600

ttttgaatct gaagccacaa ggctgcgaaa ataggagtgt atttttcctt catctaatag    660

ctcttcattg ttcttgcaga atgcatttga aattacatac ttcttttgga tttgggtaaa    720

gattgtctcc atttcaaaat ttgaaaaact gttttacggc acagctataa tttctctgat    780

gatgctgaac ttttgtgcag tacgaattcg ggttgagatc ctgcttccat gacaactttg    840

agcttatcat cgccagagtc tgccttgggg ttgtcgttca attcatgtgc agctatatca    900

cacttccact ctatgctctc gtatctcaga tgggttcaca gatgaagaga acgattttcg    960

acgagcagac ggcgaaggcc ctgaagaaat ggcacaaggc agcagtggtg aagaagaagc   1020

agcagaaggg gtcatcccat gagccaggtt cagagacacc gggcacggag acgacgacga   1080

cgacggcgac ggcaacggag gagagccagc gagaacgcga cgccgcggcc atgccggtgc   1140

gccacctcca ccgctacaag accatcgccc acgtcggcgc gacggggacg ctgtccgact   1200

cggactgctc cgacacggac acgccgttcg cgtcgccgac gaggctcctg ataccgccga   1260

caaagcagcg gagcctcgac gccgggaggg cggaggtgcg cgtggacgtc gactcgacgc   1320

cgacgccgac accaccggag cgccatgaca gcttctcctt cccgaggttg cctgctcaca   1380

atttgcagca gaaatgacca aatgatcatc catcctaagt tcctaaccat cagtagtagt   1440

agtagcagca tcaactatac atgtaattga aattgatggt ggtgacaagt gtgtgtagag   1500

cagtggagtc tgaaacttgg tgctgtccca tttggtccag ctcctactct gtgggtggag   1560

cggagctgag aaaatgccat ttcacgtaaa aaaaaaaaaa                          1600


<210> SEQ ID NO 2
<211> LENGTH: 290
<212> TYPE: PRT
<213> ORGANISM: Oryza sativa

<400> SEQUENCE: 2

Ala Ile Met Leu Phe Asn Val His Gly Trp His Asn Leu Phe Trp Phe
1               5                   10                  15

Ser Thr Ile Pro Leu Val Val Thr Leu Ala Val Gly Thr Lys Leu Gln
            20                  25                  30

Ala Ile Ile Ala Met Met Ala Val Glu Ile Lys Glu Arg His Thr Val
        35                  40                  45

Ile Gln Gly Met Pro Val Val Lys Leu Ser Asp Glu His Phe Trp Phe
    50                  55                  60

Gly Lys Pro Arg Leu Val Leu His Leu Ile His Phe Ala Ser Phe Gln
65                  70                  75                  80

Asn Ala Phe Glu Ile Thr Tyr Phe Phe Trp Ile Trp Tyr Glu Phe Gly
                85                  90                  95

Leu Arg Ser Cys Phe His Asp Asn Phe Glu Leu Ile Ile Ala Arg Val
            100                 105                 110

Cys Leu Gly Val Val Val Gln Phe Met Cys Ser Tyr Ile Thr Leu Pro
        115                 120                 125

Leu Tyr Ala Leu Val Ser Gln Met Gly Ser Gln Met Lys Arg Thr Ile
    130                 135                 140

Phe Asp Glu Gln Thr Ala Lys Ala Leu Lys Lys Trp His Lys Ala Ala
145                 150                 155                 160

Val Val Lys Lys Lys Gln Gln Lys Gly Ser Ser His Glu Pro Gly Ser
                165                 170                 175
```

-continued

```
Glu Thr Pro Gly Thr Glu Thr Thr Thr Thr Thr Ala Thr Ala Thr Glu
            180                 185                 190

Glu Ser Gln Arg Glu Arg Asp Ala Ala Ala Met Pro Val Arg His Leu
        195                 200                 205

His Arg Tyr Lys Thr Ile Ala His Val Gly Ala Thr Gly Thr Leu Ser
    210                 215                 220

Asp Ser Asp Cys Ser Asp Thr Asp Thr Pro Phe Ala Ser Pro Thr Arg
225                 230                 235                 240

Leu Leu Ile Pro Pro Thr Lys Gln Arg Ser Leu Asp Ala Gly Arg Ala
                245                 250                 255

Glu Val Arg Val Asp Val Asp Ser Thr Pro Thr Pro Thr Pro Pro Glu
            260                 265                 270

Arg His Asp Ser Phe Ser Phe Pro Arg Leu Pro Ala His Asn Leu Gln
        275                 280                 285

Gln Lys
    290


<210> SEQ ID NO 3
<211> LENGTH: 501
<212> TYPE: DNA
<213> ORGANISM: Oryza sativa
<220> FEATURE:
<221> NAME/KEY: unsure
<222> LOCATION: (335)
<223> OTHER INFORMATION: n = A, C, G, or T
<220> FEATURE:
<221> NAME/KEY: unsure
<222> LOCATION: (415)
<223> OTHER INFORMATION: n = A, C, G, or T
<220> FEATURE:
<221> NAME/KEY: unsure
<222> LOCATION: (445)
<223> OTHER INFORMATION: n = A, C, G, or T
<220> FEATURE:
<221> NAME/KEY: unsure
<222> LOCATION: (479)
<223> OTHER INFORMATION: n = A, C, G, or T
<220> FEATURE:
<221> NAME/KEY: unsure
<222> LOCATION: (482)
<223> OTHER INFORMATION: n = A, C, G, or T
<220> FEATURE:
<221> NAME/KEY: unsure
<222> LOCATION: (493)
<223> OTHER INFORMATION: n = A, C, G, or T

<400> SEQUENCE: 3

aaaatttctc tccccgcact ctctacgcgg cggcgtgcac gttctcctcc acctccgtgc     60

actatttact tcccagtttg agtttgacat tctcgcggga agaaggagaa gaagttggtg    120

agcctgtgag aggctgattg cgcggcggcc atggccggag ggggagggaa ggcggcggcg    180

ggcggcggcg aagcgccggc gataacgctg gagcacacac cgacgtggat cgtctccgcc    240

gtctgcttcg tcatcgtcat catctcgctg ctcttcgagc gcctgctcca ccgcctgggc    300

aagaggttga agaagaccgc aagaaccgct ctacnaggga ccctcaagtc aaagaagact    360

gatgctgctg ggtcatctc gctgctgctg aagtttccag ggctgacgca gaagnagctg    420

aagcacctca tggacactgc agcgncaact cgactcaggg cccaagacgc aagacacgnc    480

anggcgcgcc ggntgagagt c                                               501


<210> SEQ ID NO 4
<211> LENGTH: 81
<212> TYPE: PRT
<213> ORGANISM: Oryza sativa
```

-continued

<220> FEATURE:
<221> NAME/KEY: UNSURE
<222> LOCATION: (62)
<223> OTHER INFORMATION: Xaa = ANY AMINO ACID

<400> SEQUENCE: 4

Met Ala Gly Gly Gly Gly Lys Ala Ala Ala Gly Gly Gly Glu Ala Pro
1 5 10 15

Ala Ile Thr Leu Glu His Thr Pro Thr Trp Ile Val Ser Ala Val Cys
20 25 30

Phe Val Ile Val Ile Ile Ser Leu Leu Phe Glu Arg Leu Leu His Arg
35 40 45

Leu Gly Lys Arg Leu Lys Lys Thr Ala Arg Thr Ala Leu Xaa Gly Thr
50 55 60

Leu Lys Ser Lys Lys Thr Asp Ala Ala Gly Val Ile Ser Leu Leu Leu
65 70 75 80

Lys

<210> SEQ ID NO 5
<211> LENGTH: 513
<212> TYPE: DNA
<213> ORGANISM: Oryza sativa
<220> FEATURE:
<221> NAME/KEY: unsure
<222> LOCATION: (425)
<223> OTHER INFORMATION: n = A, C, G, or T
<220> FEATURE:
<221> NAME/KEY: unsure
<222> LOCATION: (492)
<223> OTHER INFORMATION: n = A, C, G, or T
<220> FEATURE:
<221> NAME/KEY: unsure
<222> LOCATION: (507)
<223> OTHER INFORMATION: n = A, C, G, or T

<400> SEQUENCE: 5
acagatggga tcaaacatga agaagaccat cttcgaggag cagacgatga aggccctgat 60
gaactggagg aagacggcga gggagaagaa gaagctccgg gacgccgacg agttcctagc 120
acagatgagc ggcgacacga cgccgagccg cggctcgtcg ccggtgcacc tgctgcacaa 180
gcaaagggtg aggtcggaag atccgccgag cgcaccggca tcgccggggt tcgccggaga 240
ggccagggac atgtacccgg tgcccgtggc gccggtggtg cggccgcatg ggtttaaccg 300
gatggacccg gataagagga gggcggcgtc ctcgtcggcc atccaagttg acatcgccga 360
ttctgatttc tccttcagtg tacaacggtg atggccgaaa ggtttctctg tacttaaagt 420
tgtanagcag caaatatagg aagtacaatg tatagttggt acactacata tagaggattt 480
agaaaagttc antcgatttt tttaagnaac aat 513

<210> SEQ ID NO 6
<211> LENGTH: 129
<212> TYPE: PRT
<213> ORGANISM: Oryza sativa

<400> SEQUENCE: 6

Gln Met Gly Ser Asn Met Lys Lys Thr Ile Phe Glu Glu Gln Thr Met
1 5 10 15

Lys Ala Leu Met Asn Trp Arg Lys Thr Ala Arg Glu Lys Lys Lys Leu
20 25 30

Arg Asp Ala Asp Glu Phe Leu Ala Gln Met Ser Gly Asp Thr Thr Pro
35 40 45

-continued

```
Ser Arg Gly Ser Ser Pro Val His Leu Leu His Lys Gln Arg Val Arg
     50                  55                  60

Ser Glu Asp Pro Pro Ser Ala Pro Ala Ser Pro Gly Phe Ala Gly Glu
 65                  70                  75                  80

Ala Arg Asp Met Tyr Pro Val Pro Val Ala Pro Val Val Arg Pro His
                 85                  90                  95

Gly Phe Asn Arg Met Asp Pro Asp Lys Arg Arg Ala Ala Ser Ser Ser
            100                 105                 110

Ala Ile Gln Val Asp Ile Ala Asp Ser Asp Phe Ser Phe Ser Val Gln
        115                 120                 125

Arg


<210> SEQ ID NO 7
<211> LENGTH: 1745
<212> TYPE: DNA
<213> ORGANISM: Glycine max

<400> SEQUENCE: 7

gcacgaggag agagattgga gagagaatga gtggcggagg agaagaggga gcaactctgg     60

agttcactcc gacgtgggtt gtggccgcct tttgcacagt catcgtcgcc atttccctcg    120

ccgctgagcg cctccttcat tatggcggaa agtttctcaa agccaaggac cagaagccgc    180

tctacgaagc tctccagaag atcaaagaag agctgatgct tttggggttc atttccctgc    240

ttttgacggt tacacaaaac ggcattacca aaatctgcgt tcgaccctct ttgacgctcc    300

acatgctccc gtgtaatctc cacgacgctc cagcaaacca cgaatctcat ttccagacat    360

ttttccctgg aacagccagg cgccttctct ctggggaaca ctccaccccc gagtccgcct    420

ctaaaattgg ttattgctct cgcaagcaca aggtgccttt attatctgtg gaagcacttc    480

accaccttca catcttcatt tttgtcctcg ctgtcgtaca cgtctccttt tccgtgctca    540

ccgttgtctt tggaggcgcc agaatacgtc agtggaaaca ctgggaagat tctattgcaa    600

aacagaacta cgagactgac cgagttctca aaccaaaggt cactcaggtt caccagcatg    660

attttatcag gggtcgtttt gctggttttg gcaaagactc tgctatagtc ggttggttgc    720

tatcctttct aaagcaattt tatggatctg tgacaaaatc agattatgtg acattgcgac    780

atggtttcat tatgacccac tgcaggacaa atccgaagtt taattttcac aagtacatga    840

ttcgtgccct cgaagatgat ttcaagcaag ttgttggtat aagttgggat ctttggctct    900

ttgtggttat cttcttgtta cttaatatca atggttggca tacgtatttc tggattgctt    960

ttattcctgt cattctttta cttgctgtgg gcactaagct ggagcacata ataacccaac   1020

tagctcatga agtacctgag aagcatgctg ccatagaagg tgatttagtt gtgcagccat   1080

cagatgaaca tttttggttt catcggcccc atgttgtcct ctttttgatt cactttatcc   1140

ttttccaaaa tgcctttgag atagcatttt ttttctggat atgggtcaca tatggatttg   1200

actcctgtat aatgggacaa gttcgataca ttgttccaag gcttgttatt ggggtattta   1260

ttcaggtact atgtagctac agcaccctgc cactgtatgc aattgttacg cagatgggaa   1320

ctcactataa gcgggcaata tttaatgatc atttgcaaca aaacattgtt ggttgggcac   1380

agaaggcgaa gaagaggaaa ggactaaaag ctgatggcaa tcctggccaa ggaagttctc   1440

aggagagtgc taatacagga atccagcttg ggtcaatttt caagaaggca actgctccag   1500

gagacagttc ttctgccccc aaagctgacg gaatcagctc agtgtagcta tttaagtgaa   1560

gatttacagt cttattttgt aaagttgctc acagattgca gttttcttta tattattttc   1620
```

-continued tttgctaaca taatgtagca ttgtgggaca tgtgtttgac ttggtgtacg cataaggtcg 1680
aagtactata tgagtagatg ctagtaatgc tattgtcatt tctaaaaaaa aaaaaaaaaa 1740
aaaaa 1745

<210> SEQ ID NO 8
<211> LENGTH: 506
<212> TYPE: PRT
<213> ORGANISM: Glycine max

<400> SEQUENCE: 8

Met Ser Gly Gly Gly Glu Glu Gly Ala Thr Leu Glu Phe Thr Pro Thr
1 5 10 15

Trp Val Val Ala Ala Phe Cys Thr Val Ile Val Ala Ile Ser Leu Ala
20 25 30

Ala Glu Arg Leu Leu His Tyr Gly Gly Lys Phe Leu Lys Ala Lys Asp
35 40 45

Gln Lys Pro Leu Tyr Glu Ala Leu Gln Lys Ile Lys Glu Glu Leu Met
50 55 60

Leu Leu Gly Phe Ile Ser Leu Leu Leu Thr Val Thr Gln Asn Gly Ile
65 70 75 80

Thr Lys Ile Cys Val Arg Pro Ser Leu Thr Leu His Met Leu Pro Cys
85 90 95

Asn Leu His Asp Ala Pro Ala Asn His Glu Ser His Phe Gln Thr Phe
100 105 110

Phe Pro Gly Thr Ala Arg Arg Leu Leu Ser Gly Glu His Ser Thr Pro
115 120 125

Glu Ser Ala Ser Lys Ile Gly Tyr Cys Ser Arg Lys His Lys Val Pro
130 135 140

Leu Leu Ser Val Glu Ala Leu His His Leu His Ile Phe Ile Phe Val
145 150 155 160

Leu Ala Val Val His Val Ser Phe Ser Val Leu Thr Val Val Phe Gly
165 170 175

Gly Ala Arg Ile Arg Gln Trp Lys His Trp Glu Asp Ser Ile Ala Lys
180 185 190

Gln Asn Tyr Glu Thr Asp Arg Val Leu Lys Pro Lys Val Thr Gln Val
195 200 205

His Gln His Asp Phe Ile Arg Gly Arg Phe Ala Gly Phe Gly Lys Asp
210 215 220

Ser Ala Ile Val Gly Trp Leu Leu Ser Phe Leu Lys Gln Phe Tyr Gly
225 230 235 240

Ser Val Thr Lys Ser Asp Tyr Val Thr Leu Arg His Gly Phe Ile Met
245 250 255

Thr His Cys Arg Thr Asn Pro Lys Phe Asn Phe His Lys Tyr Met Ile
260 265 270

Arg Ala Leu Glu Asp Asp Phe Lys Gln Val Val Gly Ile Ser Trp Asp
275 280 285

Leu Trp Leu Phe Val Val Ile Phe Leu Leu Leu Asn Ile Asn Gly Trp
290 295 300

His Thr Tyr Phe Trp Ile Ala Phe Ile Pro Val Ile Leu Leu Leu Ala
305 310 315 320

Val Gly Thr Lys Leu Glu His Ile Ile Thr Gln Leu Ala His Glu Val
325 330 335

Pro Glu Lys His Ala Ala Ile Glu Gly Asp Leu Val Val Gln Pro Ser
340 345 350

-continued

```
Asp Glu His Phe Trp Phe His Arg Pro His Val Val Leu Phe Leu Ile
        355                 360                 365

His Phe Ile Leu Phe Gln Asn Ala Phe Glu Ile Ala Phe Phe Phe Trp
    370                 375                 380

Ile Trp Val Thr Tyr Gly Phe Asp Ser Cys Ile Met Gly Gln Val Arg
385                 390                 395                 400

Tyr Ile Val Pro Arg Leu Val Ile Gly Val Phe Ile Gln Val Leu Cys
                405                 410                 415

Ser Tyr Ser Thr Leu Pro Leu Tyr Ala Ile Val Thr Gln Met Gly Thr
            420                 425                 430

His Tyr Lys Arg Ala Ile Phe Asn Asp His Leu Gln Gln Asn Ile Val
        435                 440                 445

Gly Trp Ala Gln Lys Ala Lys Lys Arg Lys Gly Leu Lys Ala Asp Gly
    450                 455                 460

Asn Pro Gly Gln Gly Ser Ser Gln Glu Ser Ala Asn Thr Gly Ile Gln
465                 470                 475                 480

Leu Gly Ser Ile Phe Lys Lys Ala Thr Ala Pro Gly Asp Ser Ser Ser
                485                 490                 495

Ala Pro Lys Ala Asp Gly Ile Ser Ser Val
            500                 505
```

<210> SEQ ID NO 9
<211> LENGTH: 563
<212> TYPE: DNA
<213> ORGANISM: Glycine max
<220> FEATURE:
<221> NAME/KEY: unsure
<222> LOCATION: (454)
<223> OTHER INFORMATION: n = A, C, G, or T
<220> FEATURE:
<221> NAME/KEY: unsure
<222> LOCATION: (504)
<223> OTHER INFORMATION: n = A, C, G, or T
<220> FEATURE:
<221> NAME/KEY: unsure
<222> LOCATION: (531)
<223> OTHER INFORMATION: n = A, C, G, or T
<220> FEATURE:
<221> NAME/KEY: unsure
<222> LOCATION: (559)
<223> OTHER INFORMATION: n = A, C, G, or T

<400> SEQUENCE: 9

```
cgtcatcaag gggcgcccg tggttgagcc cagcaacaag ttcttctggt tccaccgccc     60

cgactgggtc ctcttcttca tacacctgac gctgttccag aatgcgtttc agatggcaca    120

tttcgtctgg acagtggcca cgcccggctt gaagaaatgc ttccatatgc acatcggtct    180

gagcatcatg aaggtcgtgc tggggctggc tcttcagttc ctctgcagct atatcacctt    240

ccccctctac gcgctcgtca cacagatggg atcgaacatg aagaggtcca tcttcgacga    300

gcagacggcc aaggcgctga ccaactggcg gaacacggcc aaggagaaga agaaggtccg    360

agacacggac atgctgatgg cgcagatgat cggcgacgcg acgcccagcc gaggcacgtc    420

gccgatgcct agccgggctt cgtcaccggt gcanctgctt cacaagggca tgggacggtc    480

cgacgattcc cagagcgcgc cganctcgcc aaggaccatg gaggaagcta nggacatgta    540

cccggttgtg gtggcgcanc ccg                                            563
```

<210> SEQ ID NO 10
<211> LENGTH: 187
<212> TYPE: PRT

-continued

<213> ORGANISM: Glycine max
<220> FEATURE:
<221> NAME/KEY: UNSURE
<222> LOCATION: (151)
<223> OTHER INFORMATION: Xaa = ANY AMINO ACID
<220> FEATURE:
<221> NAME/KEY: UNSURE
<222> LOCATION: (168)
<223> OTHER INFORMATION: Xaa = ANY AMINO ACID
<220> FEATURE:
<221> NAME/KEY: UNSURE
<222> LOCATION: (177)
<223> OTHER INFORMATION: Xaa = ANY AMINO ACID
<220> FEATURE:
<221> NAME/KEY: UNSURE
<222> LOCATION: (186)
<223> OTHER INFORMATION: Xaa = ANY AMINO ACID

<400> SEQUENCE: 10

```
Val Ile Lys Gly Ala Pro Val Val Glu Pro Ser Asn Lys Phe Phe Trp
  1               5                  10                  15

Phe His Arg Pro Asp Trp Val Leu Phe Phe Ile His Leu Thr Leu Phe
             20                  25                  30

Gln Asn Ala Phe Gln Met Ala His Phe Val Trp Thr Val Ala Thr Pro
         35                  40                  45

Gly Leu Lys Lys Cys Phe His Met His Ile Gly Leu Ser Ile Met Lys
     50                  55                  60

Val Val Leu Gly Leu Ala Leu Gln Phe Leu Cys Ser Tyr Ile Thr Phe
 65                  70                  75                  80

Pro Leu Tyr Ala Leu Val Thr Gln Met Gly Ser Asn Met Lys Arg Ser
                 85                  90                  95

Ile Phe Asp Glu Gln Thr Ala Lys Ala Leu Thr Asn Trp Arg Asn Thr
            100                 105                 110

Ala Lys Glu Lys Lys Lys Val Arg Asp Thr Asp Met Leu Met Ala Gln
        115                 120                 125

Met Ile Gly Asp Ala Thr Pro Ser Arg Gly Thr Ser Pro Met Pro Ser
    130                 135                 140

Arg Ala Ser Ser Pro Val Xaa Leu Leu His Lys Gly Met Gly Arg Ser
145                 150                 155                 160

Asp Asp Ser Gln Ser Ala Pro Xaa Ser Pro Arg Thr Met Glu Glu Ala
                165                 170                 175

Xaa Asp Met Tyr Pro Val Val Val Ala Xaa Pro
            180                 185
```

<210> SEQ ID NO 11
<211> LENGTH: 1938
<212> TYPE: DNA
<213> ORGANISM: Glycine max
<220> FEATURE:
<221> NAME/KEY: unsure
<222> LOCATION: (1370)
<223> OTHER INFORMATION: n = A, C, G, or T

<400> SEQUENCE: 11

```
acacataaaa cctgtttcta agttcttaca acccagtttt ctccttcatt ctagtctagt     60

ctttttcttc tttttttccc ccatgtatag ctccaagttc agaaagctgt tttgttctgt    120

gttgttttca tggctctgtt ttggaggttt ggccatggca gcaggtgaaa gtagcagcag    180

ctccagagac ctagaccaga caccaacgtg ggccgttgct gctgtctgta ctgttttcat    240

cttggtatcc atagcactcg aaaagagtct ccacaaagtt gggacgtggc ttggacaaaa    300

gaaaaagaag gctttgcttg aagctctgga gaaggtcaag gctgagttga tgattttagg    360
```

-continued

```
tttcatttca ctgcttttga ctttcgggca gagttacatt gtcagaatat gtattcccga    420
aaagctggca gacaatatgt taccatgtcc gtataaatat aaggaggaca aaaaggcatc    480
agatagtgaa gaggaacatc gtaggaaact tttatcttat gaacgtagat atttagctgc    540
tgatactacc tcgttcaaat gcagcaggga gggacacgag ccacttttat ctgtcaatgg    600
attgcaccag ttacacatcc tccgtatcct cttagcagtc attcatgtgc tttacagtgc    660
tattacaatg atgcttggaa gactaaagat acttggatgg aaggcatggg aagcgggact    720
tcaactccat aattatgagt tcgccaatgc tgcttccaaa attaaactta tcatggaaac    780
atcattcgtg aggagcccca tccagttttt gattaggatt cccatcttct tctacattcg    840
ctgcttcttt aggcagttct ataggtctgt aaataggact gactacctca ctttgcgcaa    900
tgggtttatc actgtccacc tggctcctgg aagtaaattt aatttcccaa agtatatcaa    960
aagatcatta gaagatgact tcaaggtggt cgtgggagtt agtcctatcc tctgggcatc   1020
agttgtagtt taccttctca tcaatgttaa tggatggcac accgtacttt gggcagcctt   1080
aattcctgtt gttataattt tggctgttgg aacaaaactt caagccatat tggcaaatat   1140
ggctcttgaa atcacggaaa gacatgcagt tgtccaagga atgcctcttg tccaaggctc   1200
agacaaatac ttttggtttg gtcagccaca gttagttcta catcttatcc attttgcttt   1260
gttccagaat gcgttccaaa taacatatat cttgtggata tggtattctt ttgggttgag   1320
aaactgtttc cgtactgact acaagcttgc agtagtaaaa gtagctctan ggatgatgct   1380
atgcctctgc agctatatca cccttccatt atatgctctt gtaactcaga tgggttcaag   1440
gatgaaaaca gcaatatttg acgagcaaac aaacaaggct ctgaagaaat ggcacatggc   1500
tgcgaagaag aagcagggag gagcagtgac gctaggaaag tcgagtgcac gaatcatgga   1560
tggaagcccc attggtaatt cttcaacagt gcactcactg gccccacact acaccgtttc   1620
aaaactactg gccactcaac ccgctcctca tcaacagcgt acgaggatca agatcaagat   1680
catgaatatg aatccgatgg tgttgagttg tctccgttgg cgtcgcaaac aacaagcttc   1740
attgtaagag ttgatcatgg cgaccaacaa caagcagaac atagacaaga tagtgaggga   1800
gaaaccaaca gtagtagtga aggtgaattc tcatttgtca aacctgaccc tgtggaaatt   1860
agaaccacca catagcatat gatcatatat tcatctctat tcttatacat aaatctttac   1920
ataaaaaaaa aaaaaaaa                                                 1938
```

<210> SEQ ID NO 12
<211> LENGTH: 530
<212> TYPE: PRT
<213> ORGANISM: Glycine max
<220> FEATURE:
<221> NAME/KEY: UNSURE
<222> LOCATION: (406)
<223> OTHER INFORMATION: Xaa = ANY AMINO ACID

<400> SEQUENCE: 12

```
Met Ala Ala Gly Glu Ser Ser Ser Ser Ser Arg Asp Leu Asp Gln Thr
  1               5                  10                  15

Pro Thr Trp Ala Val Ala Ala Val Cys Thr Val Phe Ile Leu Val Ser
             20                  25                  30

Ile Ala Leu Glu Lys Ser Leu His Lys Val Gly Thr Trp Leu Gly Gln
         35                  40                  45

Lys Lys Lys Lys Ala Leu Leu Glu Ala Leu Glu Lys Val Lys Ala Glu
     50                  55                  60
```

-continued

```
Leu Met Ile Leu Gly Phe Ile Ser Leu Leu Leu Thr Phe Gly Gln Ser
 65                 70                  75                  80

Tyr Ile Val Arg Ile Cys Ile Pro Glu Lys Leu Ala Asp Asn Met Leu
                85                  90                  95

Pro Cys Pro Tyr Lys Tyr Lys Glu Asp Lys Lys Ala Ser Asp Ser Glu
            100                 105                 110

Glu Glu His Arg Arg Lys Leu Leu Ser Tyr Glu Arg Arg Tyr Leu Ala
        115                 120                 125

Ala Asp Thr Thr Ser Phe Lys Cys Ser Arg Glu Gly His Glu Pro Leu
    130                 135                 140

Leu Ser Val Asn Gly Leu His Gln Leu His Ile Leu Arg Ile Leu Leu
145                 150                 155                 160

Ala Val Ile His Val Leu Tyr Ser Ala Ile Thr Met Met Leu Gly Arg
                165                 170                 175

Leu Lys Ile Leu Gly Trp Lys Ala Trp Glu Ala Gly Leu Gln Leu His
            180                 185                 190

Asn Tyr Glu Phe Ala Asn Ala Ala Ser Lys Ile Lys Leu Ile Met Glu
        195                 200                 205

Thr Ser Phe Val Arg Ser Pro Ile Gln Phe Leu Ile Arg Ile Pro Ile
    210                 215                 220

Phe Phe Tyr Ile Arg Cys Phe Phe Arg Gln Phe Tyr Arg Ser Val Asn
225                 230                 235                 240

Arg Thr Asp Tyr Leu Thr Leu Arg Asn Gly Phe Ile Thr Val His Leu
                245                 250                 255

Ala Pro Gly Ser Lys Phe Asn Phe Pro Lys Tyr Ile Lys Arg Ser Leu
            260                 265                 270

Glu Asp Asp Phe Lys Val Val Val Gly Val Ser Pro Ile Leu Trp Ala
        275                 280                 285

Ser Val Val Val Tyr Leu Leu Ile Asn Val Asn Gly Trp His Thr Val
    290                 295                 300

Leu Trp Ala Ala Leu Ile Pro Val Val Ile Ile Leu Ala Val Gly Thr
305                 310                 315                 320

Lys Leu Gln Ala Ile Leu Ala Asn Met Ala Leu Glu Ile Thr Glu Arg
                325                 330                 335

His Ala Val Val Gln Gly Met Pro Leu Val Gln Gly Ser Asp Lys Tyr
            340                 345                 350

Phe Trp Phe Gly Gln Pro Gln Leu Val Leu His Leu Ile His Phe Ala
        355                 360                 365

Leu Phe Gln Asn Ala Phe Gln Ile Thr Tyr Ile Leu Trp Ile Trp Tyr
    370                 375                 380

Ser Phe Gly Leu Arg Asn Cys Phe Arg Thr Asp Tyr Lys Leu Ala Val
385                 390                 395                 400

Val Lys Val Ala Leu Xaa Met Met Leu Cys Leu Cys Ser Tyr Ile Thr
                405                 410                 415

Leu Pro Leu Tyr Ala Leu Val Thr Gln Met Gly Ser Arg Met Lys Thr
            420                 425                 430

Ala Ile Phe Asp Glu Gln Thr Asn Lys Ala Leu Lys Lys Trp His Met
        435                 440                 445

Ala Ala Lys Lys Lys Gln Gly Gly Ala Val Thr Leu Gly Lys Ser Ser
    450                 455                 460

Ala Arg Ile Met Asp Gly Ser Pro Ile Gly Asn Ser Ser Thr Val His
465                 470                 475                 480

Ser Leu Ala Pro His Tyr Thr Val Ser Lys Leu Leu Ala Thr Gln Pro
```

-continued

```
            485                 490                 495

Ala Pro His Gln Gln Arg Thr Arg Ile Lys Ile Lys Ile Met Asn Met
            500                 505                 510

Asn Pro Met Val Leu Ser Cys Leu Arg Trp Arg Arg Lys Gln Gln Ala
        515                 520                 525

Ser Leu
    530


<210> SEQ ID NO 13
<211> LENGTH: 357
<212> TYPE: DNA
<213> ORGANISM: Glycine max

<400> SEQUENCE: 13

gcacgagggg atatagagag aggtttagaa gagtgaagag aaaatgggtg gtggaggtga      60

agaagggaac aatttggaat tcactcccac ttgggttgtt gctgttgttt gttctgtgat     120

tgttgctgct tcgtttgctg ctgaaaggtt tcttcattat ggagggaagt ttctcaagag     180

gaagaatcag aagccactct atgaagccct ggaaaaaatc aaagaagagt tgatgctgtt     240

gggctttatt tctctgctac tgacaataac acaaaatggg atcatcagaa tttgtgttcc     300

agtgggttgg actcaccata tgcttccttg cagtctaaag gataaaaaaa aaaaaaa        357


<210> SEQ ID NO 14
<211> LENGTH: 104
<212> TYPE: PRT
<213> ORGANISM: Glycine max

<400> SEQUENCE: 14

Met Gly Gly Gly Gly Glu Glu Gly Asn Asn Leu Glu Phe Thr Pro Thr
  1               5                  10                  15

Trp Val Val Ala Val Val Cys Ser Val Ile Val Ala Ala Ser Phe Ala
             20                  25                  30

Ala Glu Arg Phe Leu His Tyr Gly Gly Lys Phe Leu Lys Arg Lys Asn
         35                  40                  45

Gln Lys Pro Leu Tyr Glu Ala Leu Glu Lys Ile Lys Glu Glu Leu Met
     50                  55                  60

Leu Leu Gly Phe Ile Ser Leu Leu Leu Thr Ile Thr Gln Asn Gly Ile
 65                  70                  75                  80

Ile Arg Ile Cys Val Pro Val Gly Trp Thr His His Met Leu Pro Cys
                 85                  90                  95

Ser Leu Lys Asp Lys Lys Lys Lys
            100


<210> SEQ ID NO 15
<211> LENGTH: 678
<212> TYPE: DNA
<213> ORGANISM: Triticum aestivum

<400> SEQUENCE: 15

gcacgagcgt catcaagggg gcgcccgtgg ttgagcccag caacaagttc ttctggttcc      60

accgccccga ctgggtcctc ttcttcatac acctgacgct gttccagaat gcgtttcaga     120

tggcacattt cgtctggaca gtggccacgc ccggcttgaa gaaatgcttc catatgcaca     180

tcggtctgag catcatgaag gtcgtgctgg ggctggctct tcagttcctc tgcagctata     240

tcaccttccc cctctacgcg ctcgtcacac agatgggatc gaacatgaag aggtccatct     300

tcgacgagca gacggccaag gcgctgacca actggcggaa cacggccaag gagaagaaga     360
```

-continued

```
aggtccgaga cacggacatg ctgatggcgc agatgatcgg cgacgcgacg cccagccgag    420

gcacgtcgcc gatgcctagc cgggcttcgt caccggtgca cctgcttcac aagggcatgg    480

gacggtccga cgatccccag agcgcgccga cctcgccaag gaccatggag gaggctaggg    540

acatgtaccc ggttgtggtg gcgcatcccg tgcacagact aaatcctgct gacaggcgga    600

ggtcggtctc ttcgtcggga ctcgaggccg acatcccagc gcagattttt ccttcaacca    660

gggatgagac caagtttt                                                  678
```

<210> SEQ ID NO 16
<211> LENGTH: 221
<212> TYPE: PRT
<213> ORGANISM: Triticum aestivum

<400> SEQUENCE: 16

```
Thr Ser Val Ile Lys Gly Ala Pro Val Val Glu Pro Ser Asn Lys Phe
  1               5                  10                  15

Phe Trp Phe His Arg Pro Asp Trp Val Leu Phe Phe Ile His Leu Thr
             20                  25                  30

Leu Phe Gln Asn Ala Phe Gln Met Ala His Phe Val Trp Thr Val Ala
         35                  40                  45

Thr Pro Gly Leu Lys Lys Cys Phe His Met His Ile Gly Leu Ser Ile
     50                  55                  60

Met Lys Val Val Leu Gly Leu Ala Leu Gln Phe Leu Cys Ser Tyr Ile
 65                  70                  75                  80

Thr Phe Pro Leu Tyr Ala Leu Val Thr Gln Met Gly Ser Asn Met Lys
                 85                  90                  95

Arg Ser Ile Phe Asp Glu Gln Thr Ala Lys Ala Leu Thr Asn Trp Arg
            100                 105                 110

Asn Thr Ala Lys Glu Lys Lys Lys Val Arg Asp Thr Asp Met Leu Met
        115                 120                 125

Ala Gln Met Ile Gly Asp Ala Thr Pro Ser Arg Gly Thr Ser Pro Met
    130                 135                 140

Pro Ser Arg Ala Ser Ser Pro Val His Leu Leu His Lys Gly Met Gly
145                 150                 155                 160

Arg Ser Asp Asp Pro Gln Ser Ala Pro Thr Ser Pro Arg Thr Met Glu
                165                 170                 175

Glu Ala Arg Asp Met Tyr Pro Val Val Val Ala His Pro Val His Arg
            180                 185                 190

Leu Asn Pro Ala Asp Arg Arg Arg Ser Val Ser Ser Ser Gly Leu Glu
        195                 200                 205

Ala Asp Ile Pro Ser Ala Asp Phe Ser Phe Asn Gln Gly
    210                 215                 220
```

<210> SEQ ID NO 17
<211> LENGTH: 1496
<212> TYPE: DNA
<213> ORGANISM: Triticum aestivum

<400> SEQUENCE: 17

```
gcacgaggag tacgtttggg gcgccatggc cggcggtgga gggaaggcca agccgctcga     60

gtacacgccg acatggatcg tggcgttggt ctgctccgtc atgatcatca tctccctgct    120

cttcgagcgc ttgctccacc gcctaggcaa gaggctgata aggagccgta agaagccgct    180

gtacgaggcc ctcctgaagg tgaaggagga gctgatgctg ctggggttca tctcgctgct    240
```

-continued

```
gctcaccgtg ttccagggtc ccatggggaa ggtgtgcgtc agcccgagcg ccatgctcca    300

cctgcagccc tgcagccgcc gccgcacgag acggaccacc tcggcgacgc cgtgttcacc    360

ggtgttccat tgggaaggtt ttggtccgcc cgagcttgtt ggagggccct cctcctccga    420

cgaatactgc ctcaagaagg acaaagtccc attactttca tctgacgcta ttcatcaatt    480

gcacatattt atctttgtgt tggcggtcac ccatttcctt ctcagtgcta ttacagttct    540

tctaggaatg gcacagacga gaaattggcg acattgggag cccaagatcc aagaaaataa    600

tggcagtgca cctcaaatga tcaagcatgt tcaagaattc aaatttattc aagaccactt    660

caaaggtcat agaaaacggt cgaggatatt tggttggatg cgttccttct tcaaacaatt    720

gtatggatcg gtcaccgagg aggactacac aacaatgaga cttggtttca tcatgaaaca    780

ctgtaaggga acaccaaaat tcaactttta tagttacatg atcagggctt tggaggttga    840

ctttaagaaa gtcgttggta ttagttggta cctttgggcc atgttgatga tattcctact    900

attgaatgtt gaagggtggt atgtctacat ttggatcacc ttggttccat tcattatgtt    960

acttatggta ggaagtaaga tggagcacat cataacggaa ttggcttatg aggttgccca   1020

gaagcacacg gctattcgag ggatttagt agtttctcct tcagataact tcttttggtt   1080

ccaccggcct aaattagttc ttctgttgat ccacatcgtg ctatttcaga atgcatttga   1140

aattgcattt ttcttctggc tcttggtgac atatggtttt aaatcatgca tcatggggaa   1200

accagcatat gttattactc gagttgtcat aagtgtaatc tgccaagtcc tttgtggtta   1260

cagcacccta ccactatacg ccgtcgtctc ccatatgggg aattccttca agaagactat   1320

atttgatgaa aatgtgactg aaggccttgt caactgggct gaaaaggcta ggagaggcac   1380

aagaacccca aataaaatta ctacagatgc aagtagttca ccaattgatg aggcaaatgg   1440

tggcgcggtt caaatgacaa atacacgggc aaactcgtcg gtggagcaag gcaacg       1496
```

<210> SEQ ID NO 18
<211> LENGTH: 450
<212> TYPE: PRT
<213> ORGANISM: Triticum aestivum

<400> SEQUENCE: 18

```
Met Ala Gly Gly Gly Gly Lys Ala Lys Pro Leu Glu Tyr Thr Pro Thr
  1               5                  10                  15

Trp Ile Val Ala Leu Val Cys Ser Val Met Ile Ile Ile Ser Leu Leu
             20                  25                  30

Phe Glu Arg Leu Leu His Arg Leu Gly Lys Arg Leu Ile Arg Ser Arg
         35                  40                  45

Lys Lys Pro Leu Tyr Glu Ala Leu Leu Lys Val Lys Glu Glu Leu Met
     50                  55                  60

Leu Leu Gly Phe Ile Ser Leu Leu Leu Thr Val Phe Gln Gly Pro Met
 65                  70                  75                  80

Gly Lys Val Cys Val Ser Pro Ser Ala Met Leu His Leu Gln Pro Cys
                 85                  90                  95

Ser Arg Arg Arg Thr Arg Arg Thr Thr Ser Ala Thr Pro Cys Ser Pro
            100                 105                 110

Val Phe His Trp Glu Gly Phe Gly Pro Pro Glu Leu Val Gly Gly Pro
        115                 120                 125

Ser Ser Ser Asp Glu Tyr Cys Leu Lys Lys Asp Lys Val Pro Leu Leu
    130                 135                 140

Ser Ser Asp Ala Ile His Gln Leu His Ile Phe Ile Phe Val Leu Ala
145                 150                 155                 160
```

-continued

```
Val Thr His Phe Leu Leu Ser Ala Ile Thr Val Leu Leu Gly Met Ala
                165                 170                 175

Gln Thr Arg Asn Trp Arg His Trp Glu Pro Lys Ile Gln Glu Asn Asn
            180                 185                 190

Gly Ser Ala Pro Gln Met Ile Lys His Val Gln Glu Phe Lys Phe Ile
        195                 200                 205

Gln Asp His Phe Lys Gly His Arg Lys Arg Ser Arg Ile Phe Gly Trp
    210                 215                 220

Met Arg Ser Phe Phe Lys Gln Leu Tyr Gly Ser Val Thr Glu Glu Asp
225                 230                 235                 240

Tyr Thr Thr Met Arg Leu Gly Phe Ile Met Lys His Cys Lys Gly Thr
                245                 250                 255

Pro Lys Phe Asn Phe Tyr Ser Tyr Met Ile Arg Ala Leu Glu Val Asp
            260                 265                 270

Phe Lys Lys Val Val Gly Ile Ser Trp Tyr Leu Trp Ala Met Leu Met
        275                 280                 285

Ile Phe Leu Leu Leu Asn Val Glu Gly Trp Tyr Val Tyr Ile Trp Ile
    290                 295                 300

Thr Leu Val Pro Phe Ile Met Leu Leu Met Val Gly Ser Lys Met Glu
305                 310                 315                 320

His Ile Ile Thr Glu Leu Ala Tyr Glu Val Ala Gln Lys His Thr Ala
                325                 330                 335

Ile Arg Gly Asp Leu Val Val Ser Pro Ser Asp Asn Phe Phe Trp Phe
            340                 345                 350

His Arg Pro Lys Leu Val Leu Leu Leu Ile His Ile Val Leu Phe Gln
        355                 360                 365

Asn Ala Phe Glu Ile Ala Phe Phe Phe Trp Leu Leu Val Thr Tyr Gly
    370                 375                 380

Phe Lys Ser Cys Ile Met Gly Lys Pro Ala Tyr Val Ile Thr Arg Val
385                 390                 395                 400

Val Ile Ser Val Ile Cys Gln Val Leu Cys Gly Tyr Ser Thr Leu Pro
                405                 410                 415

Leu Tyr Ala Val Val Ser His Met Gly Asn Ser Phe Lys Lys Thr Ile
            420                 425                 430

Phe Asp Glu Asn Val Thr Glu Gly Leu Val Asn Trp Ala Glu Lys Ala
        435                 440                 445

Arg Arg
    450


<210> SEQ ID NO 19
<211> LENGTH: 474
<212> TYPE: DNA
<213> ORGANISM: Triticum aestivum
<220> FEATURE:
<221> NAME/KEY: unsure
<222> LOCATION: (292)
<223> OTHER INFORMATION: n = A, C, G, or T
<220> FEATURE:
<221> NAME/KEY: unsure
<222> LOCATION: (366)
<223> OTHER INFORMATION: n = A, C, G, or T
<220> FEATURE:
<221> NAME/KEY: unsure
<222> LOCATION: (372)
<223> OTHER INFORMATION: n = A, C, G, or T
<220> FEATURE:
<221> NAME/KEY: unsure
<222> LOCATION: (383)
<223> OTHER INFORMATION: n = A, C, G, or T
```

-continued

<220> FEATURE:
<221> NAME/KEY: unsure
<222> LOCATION: (410)
<223> OTHER INFORMATION: n = A, C, G, or T
<220> FEATURE:
<221> NAME/KEY: unsure
<222> LOCATION: (418)
<223> OTHER INFORMATION: n = A, C, G, or T
<220> FEATURE:
<221> NAME/KEY: unsure
<222> LOCATION: (428)
<223> OTHER INFORMATION: n = A, C, G, or T
<220> FEATURE:
<221> NAME/KEY: unsure
<222> LOCATION: (441)
<223> OTHER INFORMATION: n = A, C, G, or T
<220> FEATURE:
<221> NAME/KEY: unsure
<222> LOCATION: (454)
<223> OTHER INFORMATION: n = A, C, G, or T
<220> FEATURE:
<221> NAME/KEY: unsure
<222> LOCATION: (468)
<223> OTHER INFORMATION: n = A, C, G, or T
<220> FEATURE:
<221> NAME/KEY: unsure
<222> LOCATION: (474)
<223> OTHER INFORMATION: n = A, C, G, or T

<400> SEQUENCE: 19
aacatatggg ttcgattcat gcatcatgga gaacagatca tatgccatcc ccagacttgc 60
tattggcatc atcgttcagg tgctctgcag ctacagcacc ctgccgctgt acgccattgt 120
cacccacatg ggcggcgaca tcaagctgca ggcgttcggc gagcacgtac acgtgtccgt 180
gcacagctgg gcgacggacg tgaagaagaa ggcgacgtcg ctgccggccc atccgcaccc 240
gcaccagcac ccgcactcgc aactccggat tccgtttctc aacaatgaag cngcacagcg 300
gaccttgacc ttgcaaccga ggaagctgca gccgcggcga agggcgacgg agcaacgcgc 360
tggaantcca antctcccac cgnaccgccg gaacaacggg ccgacactan aggaattngt 420
gacacaangg gggagacatc ntctcgaacg ccanttccct acggctanat cccn 474

<210> SEQ ID NO 20
<211> LENGTH: 133
<212> TYPE: PRT
<213> ORGANISM: Triticum aestivum
<220> FEATURE:
<221> NAME/KEY: UNSURE
<222> LOCATION: (122)
<223> OTHER INFORMATION: Xaa = ANY AMINO ACID
<220> FEATURE:
<221> NAME/KEY: UNSURE
<222> LOCATION: (124)
<223> OTHER INFORMATION: Xaa = ANY AMINO ACID
<220> FEATURE:
<221> NAME/KEY: UNSURE
<222> LOCATION: (128)
<223> OTHER INFORMATION: Xaa = ANY AMINO ACID

<400> SEQUENCE: 20

Thr Tyr Gly Phe Asp Ser Cys Ile Met Glu Asn Arg Ser Tyr Ala Ile
1 5 10 15

Pro Arg Leu Ala Ile Gly Ile Ile Val Gln Val Leu Cys Ser Tyr Ser
20 25 30

Thr Leu Pro Leu Tyr Ala Ile Val Thr His Met Gly Gly Asp Ile Lys
35 40 45

Leu Gln Ala Phe Gly Glu His Val His Val Ser Val His Ser Trp Ala
50 55 60

-continued

```
Thr Asp Val Lys Lys Lys Ala Thr Ser Leu Pro Ala His Pro His Pro
 65                  70                  75                  80

His Gln His Pro His Ser Gln Leu Arg Ile Pro Phe Leu Asn Asn Glu
                 85                  90                  95

Ala Ala Gln Arg Thr Leu Thr Leu Gln Pro Arg Lys Leu Gln Pro Arg
            100                 105                 110

Arg Arg Ala Thr Glu Gln Arg Ala Gly Xaa Pro Xaa Leu Pro Pro Xaa
        115                 120                 125

Arg Arg Asn Asn Gly
    130
```

<210> SEQ ID NO 21
<211> LENGTH: 548
<212> TYPE: DNA
<213> ORGANISM: Oryza sativa
<220> FEATURE:
<221> NAME/KEY: unsure
<222> LOCATION: (516)
<223> OTHER INFORMATION: n = A, C, G, or T
<220> FEATURE:
<221> NAME/KEY: unsure
<222> LOCATION: (526)
<223> OTHER INFORMATION: n = A, C, G, or T
<220> FEATURE:
<221> NAME/KEY: unsure
<222> LOCATION: (545)
<223> OTHER INFORMATION: n = A, C, G, or T

<400> SEQUENCE: 21

```
cttacatgta agctcgtgcc gaattcggca cgagcttaca gatacatggt acgagctttg     60

gaagcagatt ttaagaaagt ggttggtata agctggtact tgtggatatt cgttatgata    120

ttcctgctgc tgaatgttaa tggttggcac acatactttt ggatctcctt cgttcccctt    180

ctacttttgc tggccgttgg caccaagcta gaacatgtca taacccaact agcccatgag    240

gttgccgaga agcactctgc aattgagggc gacttggttg tgaatccatc agacgagcac    300

ttttggtttg gacggccgaa ggtgatccta tacctgatcc attttatcct cttccaaaac    360

gcgttcgaga tcgcgttctt cttctggatt ctgaccacct acggtttcaa ctcctgcatc    420

aagggaccaa cgtccctttt atcctgacaa ggcttatcat cgggggcatc gttcaaatcc    480

tctgcaacta caagtacctt gcctaatata tgcaantgtc acacanatgg ggctcccttt    540

ttaanaaa                                                             548
```

<210> SEQ ID NO 22
<211> LENGTH: 156
<212> TYPE: PRT
<213> ORGANISM: Oryza sativa

<400> SEQUENCE: 22

```
Tyr Arg Tyr Met Val Arg Ala Leu Glu Ala Asp Phe Lys Lys Val Val
  1               5                  10                  15

Gly Ile Ser Trp Tyr Leu Trp Ile Phe Val Met Ile Phe Leu Leu Leu
             20                  25                  30

Asn Val Asn Gly Trp His Thr Tyr Phe Trp Ile Ser Phe Val Pro Leu
         35                  40                  45

Leu Leu Leu Leu Ala Val Gly Thr Lys Leu Glu His Val Ile Thr Gln
     50                  55                  60

Leu Ala His Glu Val Ala Glu Lys His Ser Ala Ile Glu Gly Asp Leu
 65                  70                  75                  80

Val Val Asn Pro Ser Asp Glu His Phe Trp Phe Gly Arg Pro Lys Val
```

-continued

```
                85                  90                  95

Ile Leu Tyr Leu Ile His Phe Ile Leu Phe Gln Asn Ala Phe Glu Ile
            100                 105                 110

Ala Phe Phe Phe Trp Ile Leu Thr Thr Tyr Gly Phe Asn Ser Cys Ile
        115                 120                 125

Lys Gly Thr Asn Val Pro Phe Ile Leu Thr Arg Leu Ile Ile Gly Gly
    130                 135                 140

Ile Val Gln Ile Leu Cys Asn Tyr Lys Tyr Leu Ala
145                 150                 155


<210> SEQ ID NO 23
<211> LENGTH: 738
<212> TYPE: DNA
<213> ORGANISM: Oryza sativa
<220> FEATURE:
<221> NAME/KEY: unsure
<222> LOCATION: (459)
<223> OTHER INFORMATION: n = A, C, G, or T
<220> FEATURE:
<221> NAME/KEY: unsure
<222> LOCATION: (600)
<223> OTHER INFORMATION: n = A, C, G, or T
<220> FEATURE:
<221> NAME/KEY: unsure
<222> LOCATION: (606)..(607)
<223> OTHER INFORMATION: n = A, C, G, or T
<220> FEATURE:
<221> NAME/KEY: unsure
<222> LOCATION: (658)
<223> OTHER INFORMATION: n = A, C, G, or T
<220> FEATURE:
<221> NAME/KEY: unsure
<222> LOCATION: (661)
<223> OTHER INFORMATION: n = A, C, G, or T
<220> FEATURE:
<221> NAME/KEY: unsure
<222> LOCATION: (672)
<223> OTHER INFORMATION: n = A, C, G, or T
<220> FEATURE:
<221> NAME/KEY: unsure
<222> LOCATION: (675)
<223> OTHER INFORMATION: n = A, C, G, or T
<220> FEATURE:
<221> NAME/KEY: unsure
<222> LOCATION: (679)
<223> OTHER INFORMATION: n = A, C, G, or T
<220> FEATURE:
<221> NAME/KEY: unsure
<222> LOCATION: (683)
<223> OTHER INFORMATION: n = A, C, G, or T
<220> FEATURE:
<221> NAME/KEY: unsure
<222> LOCATION: (696)
<223> OTHER INFORMATION: n = A, C, G, or T
<220> FEATURE:
<221> NAME/KEY: unsure
<222> LOCATION: (707)
<223> OTHER INFORMATION: n = A, C, G, or T
<220> FEATURE:
<221> NAME/KEY: unsure
<222> LOCATION: (721)
<223> OTHER INFORMATION: n = A, C, G, or T

<400> SEQUENCE: 23

cttacaacat acttctggct gtctttcttg cccttaattc tcctactcat tgttggcaca     60

aagctggagc tcataagcac taggctggca caagaggcag cagactgccc agatgaagca    120

acaggaaacc cctggacaaa gccatgcaag gagcacttct ggttcagcaa gcctaggatt    180

gtcctccatt tgatccactt catcctgttc cagaactcct ttgagatggg ttttttcttc    240

tgggttctgg caacatatgg gtttgattca tgcatcatgg agaacaagat ttatgccctc    300
```

-continued

```
cccagacttg ctattggaat catcgtccag gtgctctgca gctacagcac gctgccgcta    360

tacgccatcg ttacccacat gggcggggac atcaagctgc aggcgttcgg cgagacggtg    420

cacgtgtcgg tgcacagctg ggcgacggac gtgaggaana agaaggcggc gccgccgccg    480

cactcccacc tccgcatccc cttcctcatg aagcgacgcc acagcacccg cggcgccgac    540

gacgccgcgg acgacgccgg cggcgacgtc gaccaccaac accaccatca cgggcaccan    600

catcanngtc accaacaaca acgaggggag ctccgtcggg ggcgggcggt ggccggtnct    660

nggagggaga tngtngccna acnacgtcct ggcggncgag gacgggncac ccggccgggc    720

nccgccgcct tttttttt                                                  738
```

<210> SEQ ID NO 24
<211> LENGTH: 155
<212> TYPE: PRT
<213> ORGANISM: Oryza sativa
<220> FEATURE:
<221> NAME/KEY: UNSURE
<222> LOCATION: (153)
<223> OTHER INFORMATION: Xaa = ANY AMINO ACID

<400> SEQUENCE: 24

```
Leu Thr Thr Tyr Phe Trp Leu Ser Phe Leu Pro Leu Ile Leu Leu Leu
  1               5                  10                  15

Ile Val Gly Thr Lys Leu Glu Leu Ile Ser Thr Arg Leu Ala Gln Glu
             20                  25                  30

Ala Ala Asp Cys Pro Asp Glu Ala Thr Gly Asn Pro Trp Thr Lys Pro
         35                  40                  45

Cys Lys Glu His Phe Trp Phe Ser Lys Pro Arg Ile Val Leu His Leu
     50                  55                  60

Ile His Phe Ile Leu Phe Gln Asn Ser Phe Glu Met Gly Phe Phe Phe
 65                  70                  75                  80

Trp Val Leu Ala Thr Tyr Gly Phe Asp Ser Cys Ile Met Glu Asn Lys
                 85                  90                  95

Ile Tyr Ala Leu Pro Arg Leu Ala Ile Gly Ile Ile Val Gln Val Leu
            100                 105                 110

Cys Ser Tyr Ser Thr Leu Pro Leu Tyr Ala Ile Val Thr His Met Gly
        115                 120                 125

Gly Asp Ile Lys Leu Gln Ala Phe Gly Glu Thr Val His Val Ser Val
    130                 135                 140

His Ser Trp Ala Thr Asp Val Arg Xaa Lys Lys
145                 150                 155
```

<210> SEQ ID NO 25
<211> LENGTH: 574
<212> TYPE: DNA
<213> ORGANISM: Oryza sativa
<220> FEATURE:
<221> NAME/KEY: unsure
<222> LOCATION: (17)
<223> OTHER INFORMATION: n = A, C, G, or T
<220> FEATURE:
<221> NAME/KEY: unsure
<222> LOCATION: (353)
<223> OTHER INFORMATION: n = A, C, G, or T
<220> FEATURE:
<221> NAME/KEY: unsure
<222> LOCATION: (437)
<223> OTHER INFORMATION: n = A, C, G, or T
<220> FEATURE:
<221> NAME/KEY: unsure
<222> LOCATION: (455)

-continued

<223> OTHER INFORMATION: n = A, C, G, or T
<220> FEATURE:
<221> NAME/KEY: unsure
<222> LOCATION: (536)
<223> OTHER INFORMATION: n = A, C, G, or T
<220> FEATURE:
<221> NAME/KEY: unsure
<222> LOCATION: (555)
<223> OTHER INFORMATION: n = A, C, G, or T
<220> FEATURE:
<221> NAME/KEY: unsure
<222> LOCATION: (557)
<223> OTHER INFORMATION: n = A, C, G, or T

<400> SEQUENCE: 25

```
atgcctacca tacgacnaac cagattacgc tcatatggcc atggaggcca gtggtttcat     60

ttccttcctg cttagcgtct tccaaaaatt tatcaatcac atttgcatcc cggagagtgc    120

tgcacatctc atgcttccat gcattactag agagacgtcc gagaccacag aagatgcttc    180

caaactttgc aagcgaaagg gtgaagttcc tatgctatct gaagaggctt tgcatcagct    240

gcacatcttt atctttgtcc ttggtattgt ccatgttgta ttttgtgtta caacattgtt    300

acttggtgga gccaagatga aaaaatggga agaaatggga gaaagaaatt cancaaggaa    360

gaaccaagga gcgaccaaag aggccaggct ggatgaaatt cattgttgta agatgtgcca    420

tctcattctt gaagcanttt tatgattctg ttggnaaacc tggattatca agtacttaag    480

atcagctttt ggtcaagagg gcactaccaa accgtcctgg attttgattt ccacangtac    540

aagggctccg tgccncntga gcatgacttt taag                                574
```

<210> SEQ ID NO 26
<211> LENGTH: 111
<212> TYPE: PRT
<213> ORGANISM: Oryza sativa
<220> FEATURE:
<221> NAME/KEY: UNSURE
<222> LOCATION: (6)
<223> OTHER INFORMATION: Xaa = ANY AMINO ACID

<400> SEQUENCE: 26

```
Cys Leu Pro Tyr Asp Xaa Pro Asp Tyr Ala His Met Ala Met Glu Ala
  1               5                  10                  15

Ser Gly Phe Ile Ser Phe Leu Leu Ser Val Phe Gln Lys Phe Ile Asn
             20                  25                  30

His Ile Cys Ile Pro Glu Ser Ala Ala His Leu Met Leu Pro Cys Ile
         35                  40                  45

Thr Arg Glu Thr Ser Glu Thr Thr Glu Asp Ala Ser Lys Leu Cys Lys
     50                  55                  60

Arg Lys Gly Glu Val Pro Met Leu Ser Glu Glu Ala Leu His Gln Leu
 65                  70                  75                  80

His Ile Phe Ile Phe Val Leu Gly Ile Val His Val Val Phe Cys Val
                 85                  90                  95

Thr Thr Leu Leu Leu Gly Gly Ala Lys Met Lys Lys Trp Glu Glu
            100                 105                 110
```

<210> SEQ ID NO 27
<211> LENGTH: 960
<212> TYPE: DNA
<213> ORGANISM: Glycine max

<400> SEQUENCE: 27

```
gcacgagggt atatgatagc aactcaatta agaagcaagc atgggaggaa aaaccttaca     60
```

-continued

```
ggaaacacct acatgggctg tggccgttgt ttgcttcgtt ttgctctcca tatctatctt    120

gatcgagcac atcctgcatc tcattggaaa gtggttgaag aagaagcaca agagagctct    180

atgcgaggca ctcgaaaaga tcaaatcaga gcttatgcta ttggggttca tatcgttgct    240

cctaacggta ggacaaggtc taatatcgag gatatgtata tcagaaaagg ttgcggggac    300

atttcacccc tgtccaaaaa aatactataa gaagaaggaa gagtcagagc accgaaccaa    360

taatggtcgg agattactag cggcttttct cgattccgat aaccaaaatc accgtcgtat    420

tttggcggcg ggaggtggtg acaactgtcc cccgggtaaa gtcccgtttg tctcatccga    480

gggtattcat caactccata tatttatctt cgtgctggct gtctttcatg tcctttactg    540

catactcact ctagctctgg gtagagcaaa gatgagaagg tggaaacgat gggaagagga    600

aaccaagaca gcacagtacc aattttcaca cgatcctgaa cgatttagat ttgcgagaga    660

aacatcattt gggagaagac acctgagttt ctgggcccaa aatcctgtcc tcctctggat    720

tgtttgtttc ttcaggcagt ttgtacggtc agttcctaaa gtggattact tgacactgag    780

gcatggattt atgatggcac atttggggcc tcatagtcac ccgaaattcg actttcggca    840

atatatcaaa agatctttgg aagaggactt caaagtggtc gttgaaatca ggtttttcgc    900

ttaattcggg ccatctatgt cttttagggt ttcttttgtt acaaaaaaaa aaaaaaaaaa    960
```

<210> SEQ ID NO 28
<211> LENGTH: 287
<212> TYPE: PRT
<213> ORGANISM: Glycine max

<400> SEQUENCE: 28

```
Met Gly Gly Lys Thr Leu Gln Glu Thr Pro Thr Trp Ala Val Ala Val
  1               5                  10                  15

Val Cys Phe Val Leu Leu Ser Ile Ser Ile Leu Ile Glu His Ile Leu
             20                  25                  30

His Leu Ile Gly Lys Trp Leu Lys Lys Lys His Lys Arg Ala Leu Cys
         35                  40                  45

Glu Ala Leu Glu Lys Ile Lys Ser Glu Leu Met Leu Leu Gly Phe Ile
     50                  55                  60

Ser Leu Leu Leu Thr Val Gly Gln Gly Leu Ile Ser Arg Ile Cys Ile
 65                  70                  75                  80

Ser Glu Lys Val Ala Gly Thr Phe His Pro Cys Pro Lys Lys Tyr Tyr
                 85                  90                  95

Lys Lys Lys Glu Glu Ser Glu His Arg Thr Asn Asn Gly Arg Arg Leu
            100                 105                 110

Leu Ala Ala Phe Leu Asp Ser Asp Asn Gln Asn His Arg Arg Ile Leu
        115                 120                 125

Ala Ala Gly Gly Gly Asp Asn Cys Pro Pro Gly Lys Val Pro Phe Val
    130                 135                 140

Ser Ser Glu Gly Ile His Gln Leu His Ile Phe Ile Phe Val Leu Ala
145                 150                 155                 160

Val Phe His Val Leu Tyr Cys Ile Leu Thr Leu Ala Leu Gly Arg Ala
                165                 170                 175

Lys Met Arg Arg Trp Lys Arg Trp Glu Glu Glu Thr Lys Thr Ala Gln
            180                 185                 190

Tyr Gln Phe Ser His Asp Pro Glu Arg Phe Arg Phe Ala Arg Glu Thr
        195                 200                 205

Ser Phe Gly Arg Arg His Leu Ser Phe Trp Ala Gln Asn Pro Val Leu
    210                 215                 220
```

-continued

```
Leu Trp Ile Val Cys Phe Phe Arg Gln Phe Val Arg Ser Val Pro Lys
225                 230                 235                 240

Val Asp Tyr Leu Thr Leu Arg His Gly Phe Met Met Ala His Leu Gly
                245                 250                 255

Pro His Ser His Pro Lys Phe Asp Phe Arg Gln Tyr Ile Lys Arg Ser
            260                 265                 270

Leu Glu Glu Asp Phe Lys Val Val Val Glu Ile Arg Phe Phe Ala
        275                 280                 285
```

<210> SEQ ID NO 29
<211> LENGTH: 476
<212> TYPE: DNA
<213> ORGANISM: Glycine max
<220> FEATURE:
<221> NAME/KEY: unsure
<222> LOCATION: (223)
<223> OTHER INFORMATION: n = A, C, G, or T
<220> FEATURE:
<221> NAME/KEY: unsure
<222> LOCATION: (248)..(249)
<223> OTHER INFORMATION: n = A, C, G, or T
<220> FEATURE:
<221> NAME/KEY: unsure
<222> LOCATION: (254)
<223> OTHER INFORMATION: n = A, C, G, or T
<220> FEATURE:
<221> NAME/KEY: unsure
<222> LOCATION: (311)
<223> OTHER INFORMATION: n = A, C, G, or T
<220> FEATURE:
<221> NAME/KEY: unsure
<222> LOCATION: (330)
<223> OTHER INFORMATION: n = A, C, G, or T
<220> FEATURE:
<221> NAME/KEY: unsure
<222> LOCATION: (341)
<223> OTHER INFORMATION: n = A, C, G, or T
<220> FEATURE:
<221> NAME/KEY: unsure
<222> LOCATION: (350)
<223> OTHER INFORMATION: n = A, C, G, or T
<220> FEATURE:
<221> NAME/KEY: unsure
<222> LOCATION: (361)
<223> OTHER INFORMATION: n = A, C, G, or T
<220> FEATURE:
<221> NAME/KEY: unsure
<222> LOCATION: (389)
<223> OTHER INFORMATION: n = A, C, G, or T
<220> FEATURE:
<221> NAME/KEY: unsure
<222> LOCATION: (405)
<223> OTHER INFORMATION: n = A, C, G, or T
<220> FEATURE:
<221> NAME/KEY: unsure
<222> LOCATION: (446)
<223> OTHER INFORMATION: n = A, C, G, or T

<400> SEQUENCE: 29

```
atgctctagt cacccagatg ggttctacca tgaaagttac tattttcaat gaaaatgttg     60

cagtagccct gaagaactgg catcacactg ctaaaaagca catcaaacac aacaaggatt    120

ctacttcaaa tacaccattc tcaagcaggc caggaacccc gacacatggc atgtctccag    180

ttcacttgct tcacaagcac cctagacaca gtgacagtcc aantatttct cccaagggca    240

tacaattnnc aaanatgaac aatggggttt ttaaagggat acattccccc caggcaacaa    300

cgcaaggaat naatgttctt attaatgaan agaccatgca nattcaaatn caagattcaa    360

naacaacggg caacttcaac agcaagatnc ctcctaatgg gaccnatccc tatccgaatc    420
```

-continued

```
aacaatgaat ccacattctt aacctnaatt cattttggaa ggggacacac acttgt        476


<210> SEQ ID NO 30
<211> LENGTH: 77
<212> TYPE: PRT
<213> ORGANISM: Glycine max
<220> FEATURE:
<221> NAME/KEY: UNSURE
<222> LOCATION: (74)
<223> OTHER INFORMATION: Xaa = ANY AMINO ACID

<400> SEQUENCE: 30

Ala Leu Val Thr Gln Met Gly Ser Thr Met Lys Val Thr Ile Phe Asn
  1               5                  10                  15

Glu Asn Val Ala Val Ala Leu Lys Asn Trp His His Thr Ala Lys Lys
             20                  25                  30

His Ile Lys His Asn Lys Asp Ser Thr Ser Asn Thr Pro Phe Ser Ser
         35                  40                  45

Arg Pro Gly Thr Pro Thr His Gly Met Ser Pro Val His Leu Leu His
     50                  55                  60

Lys His Pro Arg His Ser Asp Ser Pro Xaa Ile Ser Pro
 65                  70                  75


<210> SEQ ID NO 31
<211> LENGTH: 1711
<212> TYPE: DNA
<213> ORGANISM: Triticum aestivum

<400> SEQUENCE: 31

atggcggagg actacgagta ccccccggcg cggacgctgc cggagacgcc gtcctgggcg     60

gtggcgctcg tcttcgccgt catgatcatc gtgtccgtcc tcctggagca cgcgctccac    120

aagctcggcc attggttcca caagcggcac aagaacgcgc tggcggaggc gctggagaag    180

atcaaagcgg agctgatgct ggtggggttc atctcgctgc tgctcgccgt gacgcaggac    240

ccaatctccg ggatatgcat ctccgagaag gccgccagca tcatgcggcc ctgcagcctg    300

ccccctggtt ccgtcaagag caagtacaaa gactactact gcgccaaaaa gggcaaggtg    360

tcgctaatgt ccacgggcag cttgcaccag ctccacatat tcatcttcgt gctcgccgtc    420

ttccatgtca cctacagcgt catcatcatg gctctaagcc gtctcaaaat gaggacatgg    480

aagaaatggg agacagagac cgcctccttg gaataccagt tcgcaaatga tcctgcgcgg    540

ttccgcttca cgcaccagac gtcgttcgtg aagcggcacc tgggcctctc cagcaccccc    600

ggcatcagat gggtggtggc cttcttcagg cagttcttca ggtcggtcac caaggtggac    660

tacctcaccc tgagggcagg cttcatcaac gcgcatttgt cgcataacag caagttcgac    720

ttccacaagt acatcaagag gtccatggag gacgacttca aagtcgtcgt tggcatcagc    780

ctcccgctgt ggtgtgtggc gatcctcacc ctcttccttg atattgacgg gatcggcacg    840

ctcacctgga tttctttcat ccctctcgtc atcctcttgt gtgttggaac caagctggag    900

atgatcatca tggagatggc cctggagatc caggaccggg cgagcgtcat caagggggcg    960

cccgtggttg agcccagcaa caagttcttc tggttccacc gccccgactg ggtcctcttc   1020

ttcatacacc tgacgctgtt ccagaatgcg tttcagatgg cacatttcgt ctggacagtg   1080

gccacgcccg gcttgaagaa atgcttccat atgcacatcg gtctgagcat catgaaggtc   1140

gtgctggggc tggctcttca gttcctctgc agctatatca ccttcccccct ctacgcgctc   1200

gtcacacaga tgggatcgaa catgaagagg tccatcttcg acgagcagac ggccaaggcg   1260
```

-continued

```
ctgaccaact ggcggaacac ggccaaggag aagaagaagg tccgagacac ggacatgctg   1320

atggcgcaga tgatcggcga cgcgacgccc agccgaggca cgtcgccgat gcctagccgg   1380

gcttcgtcac cggtgcacct gcttcacaag ggcatgggac ggtccgacga tccccagagc   1440

gcgccgacct cgccaaggac catggaggag gctagggaca tgtacccggt tgtggtggcg   1500

catcccgtgc acagactaaa tcctgctgac aggcggaggt cggtctcttc gtcggcactc   1560

gatgccgaca tccccagcgc agatttttcc ttcagccagg gatgagacaa gtttatgtat   1620

tgatgttagt ccaatgtata gccaacatag gatgtcatga ttcgtacaat aagaaataga   1680

attttttact gagtcaaaaa aaaaaaaaaa a                                  1711
```

```
<210> SEQ ID NO 32
<211> LENGTH: 534
<212> TYPE: PRT
<213> ORGANISM: Triticum aestivum

<400> SEQUENCE: 32

Met Ala Glu Asp Tyr Glu Tyr Pro Pro Ala Arg Thr Leu Pro Glu Thr
  1               5                  10                  15

Pro Ser Trp Ala Val Ala Leu Val Phe Ala Val Met Ile Ile Val Ser
             20                  25                  30

Val Leu Leu Glu His Ala Leu His Lys Leu Gly His Trp Phe His Lys
         35                  40                  45

Arg His Lys Asn Ala Leu Ala Glu Ala Leu Glu Lys Ile Lys Ala Glu
     50                  55                  60

Leu Met Leu Val Gly Phe Ile Ser Leu Leu Leu Ala Val Thr Gln Asp
 65                  70                  75                  80

Pro Ile Ser Gly Ile Cys Ile Ser Glu Lys Ala Ala Ser Ile Met Arg
                 85                  90                  95

Pro Cys Ser Leu Pro Pro Gly Ser Val Lys Ser Lys Tyr Lys Asp Tyr
            100                 105                 110

Tyr Cys Ala Lys Lys Gly Lys Val Ser Leu Met Ser Thr Gly Ser Leu
        115                 120                 125

His Gln Leu His Ile Phe Ile Phe Val Leu Ala Val Phe His Val Thr
    130                 135                 140

Tyr Ser Val Ile Ile Met Ala Leu Ser Arg Leu Lys Met Arg Thr Trp
145                 150                 155                 160

Lys Lys Trp Glu Thr Glu Thr Ala Ser Leu Glu Tyr Gln Phe Ala Asn
                165                 170                 175

Asp Pro Ala Arg Phe Arg Phe Thr His Gln Thr Ser Phe Val Lys Arg
            180                 185                 190

His Leu Gly Leu Ser Ser Thr Pro Gly Ile Arg Trp Val Val Ala Phe
        195                 200                 205

Phe Arg Gln Phe Phe Arg Ser Val Thr Lys Val Asp Tyr Leu Thr Leu
    210                 215                 220

Arg Ala Gly Phe Ile Asn Ala His Leu Ser His Asn Ser Lys Phe Asp
225                 230                 235                 240

Phe His Lys Tyr Ile Lys Arg Ser Met Glu Asp Asp Phe Lys Val Val
                245                 250                 255

Val Gly Ile Ser Leu Pro Leu Trp Cys Val Ala Ile Leu Thr Leu Phe
            260                 265                 270

Leu Asp Ile Asp Gly Ile Gly Thr Leu Thr Trp Ile Ser Phe Ile Pro
        275                 280                 285

Leu Val Ile Leu Leu Cys Val Gly Thr Lys Leu Glu Met Ile Ile Met
```

-continued

```
    290                 295                 300

Glu Met Ala Leu Glu Ile Gln Asp Arg Ala Ser Val Ile Lys Gly Ala
305                 310                 315                 320

Pro Val Val Glu Pro Ser Asn Lys Phe Phe Trp Phe His Arg Pro Asp
                325                 330                 335

Trp Val Leu Phe Phe Ile His Leu Thr Leu Phe Gln Asn Ala Phe Gln
            340                 345                 350

Met Ala His Phe Val Trp Thr Val Ala Thr Pro Gly Leu Lys Lys Cys
        355                 360                 365

Phe His Met His Ile Gly Leu Ser Ile Met Lys Val Val Leu Gly Leu
    370                 375                 380

Ala Leu Gln Phe Leu Cys Ser Tyr Ile Thr Phe Pro Leu Tyr Ala Leu
385                 390                 395                 400

Val Thr Gln Met Gly Ser Asn Met Lys Arg Ser Ile Phe Asp Glu Gln
                405                 410                 415

Thr Ala Lys Ala Leu Thr Asn Trp Arg Asn Thr Ala Lys Glu Lys Lys
            420                 425                 430

Lys Val Arg Asp Thr Asp Met Leu Met Ala Gln Met Ile Gly Asp Ala
        435                 440                 445

Thr Pro Ser Arg Gly Thr Ser Pro Met Pro Ser Arg Ala Ser Ser Pro
    450                 455                 460

Val His Leu Leu His Lys Gly Met Gly Arg Ser Asp Asp Pro Gln Ser
465                 470                 475                 480

Ala Pro Thr Ser Pro Arg Thr Met Glu Glu Ala Arg Asp Met Tyr Pro
                485                 490                 495

Val Val Val Ala His Pro Val His Arg Leu Asn Pro Ala Asp Arg Arg
            500                 505                 510

Arg Ser Val Ser Ser Ser Ala Leu Asp Ala Asp Ile Pro Ser Ala Asp
        515                 520                 525

Phe Ser Phe Ser Gln Gly
    530
```

<210> SEQ ID NO 33
<211> LENGTH: 482
<212> TYPE: DNA
<213> ORGANISM: Triticum aestivum
<220> FEATURE:
<221> NAME/KEY: unsure
<222> LOCATION: (81)
<223> OTHER INFORMATION: n = A, C, G, or T
<220> FEATURE:
<221> NAME/KEY: unsure
<222> LOCATION: (177)
<223> OTHER INFORMATION: n = A, C, G, or T
<220> FEATURE:
<221> NAME/KEY: unsure
<222> LOCATION: (280)
<223> OTHER INFORMATION: n = A, C, G, or T
<220> FEATURE:
<221> NAME/KEY: unsure
<222> LOCATION: (336)
<223> OTHER INFORMATION: n = A, C, G, or T
<220> FEATURE:
<221> NAME/KEY: unsure
<222> LOCATION: (339)
<223> OTHER INFORMATION: n = A, C, G, or T
<220> FEATURE:
<221> NAME/KEY: unsure
<222> LOCATION: (345)
<223> OTHER INFORMATION: n = A, C, G, or T
<220> FEATURE:
<221> NAME/KEY: unsure
<222> LOCATION: (350)

-continued

<223> OTHER INFORMATION: n = A, C, G, or T
<220> FEATURE:
<221> NAME/KEY: unsure
<222> LOCATION: (371)
<223> OTHER INFORMATION: n = A, C, G, or T
<220> FEATURE:
<221> NAME/KEY: unsure
<222> LOCATION: (380)
<223> OTHER INFORMATION: n = A, C, G, or T
<220> FEATURE:
<221> NAME/KEY: unsure
<222> LOCATION: (399)
<223> OTHER INFORMATION: n = A, C, G, or T
<220> FEATURE:
<221> NAME/KEY: unsure
<222> LOCATION: (405)
<223> OTHER INFORMATION: n = A, C, G, or T
<220> FEATURE:
<221> NAME/KEY: unsure
<222> LOCATION: (412)
<223> OTHER INFORMATION: n = A, C, G, or T
<220> FEATURE:
<221> NAME/KEY: unsure
<222> LOCATION: (432)
<223> OTHER INFORMATION: n = A, C, G, or T
<220> FEATURE:
<221> NAME/KEY: unsure
<222> LOCATION: (452)
<223> OTHER INFORMATION: n = A, C, G, or T
<220> FEATURE:
<221> NAME/KEY: unsure
<222> LOCATION: (462)
<223> OTHER INFORMATION: n = A, C, G, or T
<220> FEATURE:
<221> NAME/KEY: unsure
<222> LOCATION: (466)
<223> OTHER INFORMATION: n = A, C, G, or T
<220> FEATURE:
<221> NAME/KEY: unsure
<222> LOCATION: (476)
<223> OTHER INFORMATION: n = A, C, G, or T
<220> FEATURE:
<221> NAME/KEY: unsure
<222> LOCATION: (482)
<223> OTHER INFORMATION: n = A, C, G, or T

<400> SEQUENCE: 33
cgcacgacct acgtagcctt cgcgtagcct gcgccttccc ttccattaat tttgctttgc 60
ctgctccggc acggcactta natagctcct tcgtccaaac gaaacgactg gtacggtgct 120
tgtgcgtgtg tctcgttgat cgatcgaggt ggtcgtttgc tcggcaccta aaaagangtt 180
gagcggcggg tcatggcggg gccggcggga gggcgggaac tgccggacac cccgacgtgg 240
gcggtggggc tcgtctgcgc cgttatgata ctcgtctccn tcgccatggg gcacgccctc 300
cacaacctcg ggcactggtt ccacaagcgg cacaanaang gcatngcggn ggcgctggag 360
aaaattaagg nggggctcan gcttggtggg gcttcatanc cctgntcctc anccgtgggg 420
caggaaccca tntccaagat atgcaatctc cntggagggg cngcancaaa gaatgntccc 480 cn 482

<210> SEQ ID NO 34
<211> LENGTH: 66
<212> TYPE: PRT
<213> ORGANISM: Triticum aestivum
<220> FEATURE:
<221> NAME/KEY: UNSURE
<222> LOCATION: (30)
<223> OTHER INFORMATION: Xaa = ANY AMINO ACID
<220> FEATURE:
<221> NAME/KEY: UNSURE
<222> LOCATION: (48)..(49)
<223> OTHER INFORMATION: Xaa = ANY AMINO ACID -continued
<220> FEATURE:
<221> NAME/KEY: UNSURE
<222> LOCATION: (51)
<223> OTHER INFORMATION: Xaa = ANY AMINO ACID
<220> FEATURE:
<221> NAME/KEY: UNSURE
<222> LOCATION: (53)
<223> OTHER INFORMATION: Xaa = ANY AMINO ACID
<220> FEATURE:
<221> NAME/KEY: UNSURE
<222> LOCATION: (60)
<223> OTHER INFORMATION: Xaa = ANY AMINO ACID
<220> FEATURE:
<221> NAME/KEY: UNSURE
<222> LOCATION: (63)
<223> OTHER INFORMATION: Xaa = ANY AMINO ACID

<400> SEQUENCE: 34

Met Ala Gly Pro Ala Gly Gly Arg Glu Leu Pro Asp Thr Pro Thr Trp
1 5 10 15

Ala Val Gly Leu Val Cys Ala Val Met Ile Leu Val Ser Xaa Ala Met
20 25 30

Gly His Ala Leu His Asn Leu Gly His Trp Phe His Lys Arg His Xaa
35 40 45

Xaa Gly Xaa Ala Xaa Ala Leu Glu Lys Ile Lys Xaa Gly Leu Xaa Leu
50 55 60

Gly Gly
65

<210> SEQ ID NO 35
<211> LENGTH: 462
<212> TYPE: DNA
<213> ORGANISM: Triticum aestivum
<220> FEATURE:
<221> NAME/KEY: unsure
<222> LOCATION: (19)
<223> OTHER INFORMATION: n = A, C, G, or T
<220> FEATURE:
<221> NAME/KEY: unsure
<222> LOCATION: (328)
<223> OTHER INFORMATION: n = A, C, G, or T
<220> FEATURE:
<221> NAME/KEY: unsure
<222> LOCATION: (382)
<223> OTHER INFORMATION: n = A, C, G, or T
<220> FEATURE:
<221> NAME/KEY: unsure
<222> LOCATION: (394)
<223> OTHER INFORMATION: n = A, C, G, or T
<220> FEATURE:
<221> NAME/KEY: unsure
<222> LOCATION: (453)
<223> OTHER INFORMATION: n = A, C, G, or T

<400> SEQUENCE: 35
gctaagatga gaacatggna taaatgggag aaagaaattc aacaaggaag actcaacgag 60
cgtgaaaaga ggccaggctg gatgaaacca tctgctgtaa gatggattat tgcattcttc 120
aagcagtttt ataattctgt cggtaaacca gattatcaag tactcagatc agcttttgtt 180
ctgcggcact acccaaatcg cccagacttt gatttccaca agtacatggt tcgtgccttg 240
aagcatgatt tcaaagaagt agttggaatc agctggtacc tatggctttt cgttatcgtc 300
ttcctgctgc tgaatataaa tgggtggnac acatacttct ggctgtcttt cttgcccttg 360
attcctctgc ttattgttgg gnactaagct gggnggtaca tcagcactcg attgggctca 420
aagaaagcaa cggatttgtt ctggatgaaa gcnatcaagg ga 462

-continued

<210> SEQ ID NO 36
<211> LENGTH: 127
<212> TYPE: PRT
<213> ORGANISM: Triticum aestivum
<220> FEATURE:
<221> NAME/KEY: UNSURE
<222> LOCATION: (7)
<223> OTHER INFORMATION: Xaa = ANY AMINO ACID
<220> FEATURE:
<221> NAME/KEY: UNSURE
<222> LOCATION: (110)
<223> OTHER INFORMATION: Xaa = ANY AMINO ACID

<400> SEQUENCE: 36

```
Ala Lys Met Arg Thr Trp Xaa Lys Trp Glu Lys Glu Ile Gln Gln Gly
  1               5                  10                  15

Arg Leu Asn Glu Arg Glu Lys Arg Pro Gly Trp Met Lys Pro Ser Ala
            20                  25                  30

Val Arg Trp Ile Ile Ala Phe Phe Lys Gln Phe Tyr Asn Ser Val Gly
        35                  40                  45

Lys Pro Asp Tyr Gln Val Leu Arg Ser Ala Phe Val Leu Arg His Tyr
    50                  55                  60

Pro Asn Arg Pro Asp Phe Asp Phe His Lys Tyr Met Val Arg Ala Leu
 65                  70                  75                  80

Lys His Asp Phe Lys Glu Val Val Gly Ile Ser Trp Tyr Leu Trp Leu
                 85                  90                  95

Phe Val Ile Val Phe Leu Leu Leu Asn Ile Asn Gly Trp Xaa Thr Tyr
            100                 105                 110

Phe Trp Leu Ser Phe Leu Pro Leu Ile Pro Leu Leu Ile Val Gly
        115                 120                 125
```

<210> SEQ ID NO 37
<211> LENGTH: 1666
<212> TYPE: DNA
<213> ORGANISM: Triticum aestivum

<400> SEQUENCE: 37

```
gcacgaggag tacgtttggg gcgccatggc cggcggtgga gggaaggcca agccgctcga     60

gtacacgccg acatggatcg tggcgttggt ctgctccgtc atgatcatca tctccctgct    120

cttcgagcgc ttgctccacc gcctaggcaa gaggctgata aggagccgta agaagccgct    180

gtacgaggcc ctcctgaagg tgaaggagga gctgatgctg ctggggttca tctcgctgct    240

gctcaccgtg ttccagggtc ccatggggaa ggtgtgcgtc agcccgagcg ccatgctcca    300

cctgcagccc tgcaagccgc cgccgcacga gacggaccac ctcggcgacg ccgtgttcac    360

cggcgtgctg ggtggggcga ggcgcctcct ggctggagga gcctcctcct ccgacaaata    420

ctgcctcaag aaggacaaag ttccattact ttcatctgac gctattcatc aattgcacat    480

atttatcttt gtgttggcgg tcacccattt ccttctcagt gctattacag ttcttctagg    540

aatggcacag acgagaaatt ggcgacattg ggagaccaag atccaagaaa ataatggcag    600

tgcacctcaa atgatcaagc atgttcaaga attcaaattt attcaagacc acttcaaagg    660

tcatagaaaa cggtcgagga tatttggttg gatgcgttcc ttcttcaaac aattgtatgg    720

atcggtcacc gaggaggact acacaacaat gagacttggt ttcatcatga aacactgtaa    780

gggaacacca aaattcaact tttatagtta catgatcagg gctttggagg ttgactttaa    840

gaaagtcgtt ggtattagtt ggtacctttg ggccatgttg atgatattcc tactattgaa    900

tgttgaaggg tggtatgtct acatttggat caccttggtt ccattcatta tgttacttat    960
```

-continued

```
ggtaggaagt aagatggagc acatcataac ggaattggct tatgaggttg cccagaagca   1020

cacggctatt cgaggggatt tagtagtttc tccttcagat aacttctttt ggttccaccg   1080

gcctaaatta gttcttctgt tgatccacat cgtgctattt cagaatgcat ttgaaattgc   1140

atttttcttc tggctcttgg tgacatatgg ttttaaatca tgcatcatgg ggaaaccagc   1200

atatgttatt actcgagttg tcataagtgt aatctgccaa gtcctttgtg gttacagcac   1260

cctaccacta tacgccgtcg tctcccatat ggggaattcc ttcaagaaga ctatatttga   1320

tgaaaatgtg actgaaggcc ttgtcaactg ggctgaaaag gctaggagag gcacaagaac   1380

cccaaataaa attactacag atgcaagtag ttcaccaatt gatgaggcaa atggtggcgc   1440

ggttcaaatg acaaatacac gggcaaactc gtcggtggag caaggcaccg ctaggttgat   1500

ataatcatgt acattagttg ctaatacaaa gggtccatgg gcaacaattt tggcaagtgg   1560

acagatttat tttttgaggg catcacatat ctttaataat gcacgggaat catgtgttcc   1620

cgtttttaaa ccaaaaagag aaataacccc cctctaaaaa gaaaca                  1666


<210> SEQ ID NO 38
<211> LENGTH: 492
<212> TYPE: PRT
<213> ORGANISM: Triticum aestivum

<400> SEQUENCE: 38

Met Ala Gly Gly Gly Gly Lys Ala Lys Pro Leu Glu Tyr Thr Pro Thr
  1               5                  10                  15

Trp Ile Val Ala Leu Val Cys Ser Val Met Ile Ile Ile Ser Leu Leu
             20                  25                  30

Phe Glu Arg Leu Leu His Arg Leu Gly Lys Arg Leu Ile Arg Ser Arg
         35                  40                  45

Lys Lys Pro Leu Tyr Glu Ala Leu Leu Lys Val Lys Glu Glu Leu Met
     50                  55                  60

Leu Leu Gly Phe Ile Ser Leu Leu Leu Thr Val Phe Gln Gly Pro Met
 65                  70                  75                  80

Gly Lys Val Cys Val Ser Pro Ser Ala Met Leu His Leu Gln Pro Cys
                 85                  90                  95

Lys Pro Pro Pro His Glu Thr Asp His Leu Gly Asp Ala Val Phe Thr
            100                 105                 110

Gly Val Leu Gly Gly Ala Arg Arg Leu Leu Ala Gly Gly Ala Ser Ser
        115                 120                 125

Ser Asp Lys Tyr Cys Leu Lys Lys Asp Lys Val Pro Leu Leu Ser Ser
    130                 135                 140

Asp Ala Ile His Gln Leu His Ile Phe Ile Phe Val Leu Ala Val Thr
145                 150                 155                 160

His Phe Leu Leu Ser Ala Ile Thr Val Leu Leu Gly Met Ala Gln Thr
                165                 170                 175

Arg Asn Trp Arg His Trp Glu Thr Lys Ile Gln Glu Asn Asn Gly Ser
            180                 185                 190

Ala Pro Gln Met Ile Lys His Val Gln Glu Phe Lys Phe Ile Gln Asp
        195                 200                 205

His Phe Lys Gly His Arg Lys Arg Ser Arg Ile Phe Gly Trp Met Arg
    210                 215                 220

Ser Phe Phe Lys Gln Leu Tyr Gly Ser Val Thr Glu Glu Asp Tyr Thr
225                 230                 235                 240

Thr Met Arg Leu Gly Phe Ile Met Lys His Cys Lys Gly Thr Pro Lys
                245                 250                 255
```

-continued

```
Phe Asn Phe Tyr Ser Tyr Met Ile Arg Ala Leu Glu Val Asp Phe Lys
            260                 265                 270

Lys Val Val Gly Ile Ser Trp Tyr Leu Trp Ala Met Leu Met Ile Phe
        275                 280                 285

Leu Leu Leu Asn Val Glu Gly Trp Tyr Val Tyr Ile Trp Ile Thr Leu
    290                 295                 300

Val Pro Phe Ile Met Leu Leu Met Val Gly Ser Lys Met Glu His Ile
305                 310                 315                 320

Ile Thr Glu Leu Ala Tyr Glu Val Ala Gln Lys His Thr Ala Ile Arg
                325                 330                 335

Gly Asp Leu Val Val Ser Pro Ser Asp Asn Phe Phe Trp Phe His Arg
            340                 345                 350

Pro Lys Leu Val Leu Leu Leu Ile His Ile Val Leu Phe Gln Asn Ala
        355                 360                 365

Phe Glu Ile Ala Phe Phe Phe Trp Leu Leu Val Thr Tyr Gly Phe Lys
    370                 375                 380

Ser Cys Ile Met Gly Lys Pro Ala Tyr Val Ile Thr Arg Val Val Ile
385                 390                 395                 400

Ser Val Ile Cys Gln Val Leu Cys Gly Tyr Ser Thr Leu Pro Leu Tyr
                405                 410                 415

Ala Val Val Ser His Met Gly Asn Ser Phe Lys Lys Thr Ile Phe Asp
            420                 425                 430

Glu Asn Val Thr Glu Gly Leu Val Asn Trp Ala Glu Lys Ala Arg Arg
        435                 440                 445

Gly Thr Arg Thr Pro Asn Lys Ile Thr Thr Asp Ala Ser Ser Ser Pro
    450                 455                 460

Ile Asp Glu Ala Asn Gly Gly Ala Val Gln Met Thr Asn Thr Arg Ala
465                 470                 475                 480

Asn Ser Ser Val Glu Gln Gly Thr Ala Arg Leu Ile
                485                 490


<210> SEQ ID NO 39
<211> LENGTH: 533
<212> TYPE: PRT
<213> ORGANISM: Hordeum vulgare

<400> SEQUENCE: 39

Met Ser Asp Lys Lys Gly Val Pro Ala Arg Glu Leu Pro Glu Thr Pro
  1               5                  10                  15

Ser Trp Ala Val Ala Val Val Phe Ala Ala Met Val Leu Val Ser Val
             20                  25                  30

Leu Met Glu His Gly Leu His Lys Leu Gly His Trp Phe Gln His Arg
         35                  40                  45

His Lys Lys Ala Leu Trp Glu Ala Leu Glu Lys Met Lys Ala Glu Leu
     50                  55                  60

Met Leu Val Gly Phe Ile Ser Leu Leu Leu Ile Val Thr Gln Asp Pro
 65                  70                  75                  80

Ile Ile Ala Lys Ile Cys Ile Ser Glu Asp Ala Ala Asp Val Met Trp
                 85                  90                  95

Pro Cys Lys Arg Gly Thr Glu Gly Arg Lys Pro Ser Lys Tyr Val Asp
            100                 105                 110

Tyr Cys Pro Glu Gly Lys Val Ala Leu Met Ser Thr Gly Ser Leu His
        115                 120                 125

Gln Leu His Val Phe Ile Phe Val Leu Ala Val Phe His Val Thr Tyr
```

-continued

```
    130                 135                 140

Ser Val Ile Thr Ile Ala Leu Ser Arg Leu Lys Met Arg Thr Trp Lys
145                 150                 155                 160

Lys Trp Glu Thr Glu Thr Thr Ser Leu Glu Tyr Gln Phe Ala Asn Asp
                165                 170                 175

Pro Ala Arg Phe Arg Phe Thr His Gln Thr Ser Phe Val Lys Arg His
            180                 185                 190

Leu Gly Leu Ser Ser Thr Pro Gly Ile Arg Trp Val Val Ala Phe Phe
        195                 200                 205

Arg Gln Phe Phe Arg Ser Val Thr Lys Val Asp Tyr Leu Thr Leu Arg
    210                 215                 220

Ala Gly Phe Ile Asn Ala His Leu Ser Gln Asn Ser Lys Phe Asp Phe
225                 230                 235                 240

His Lys Tyr Ile Lys Arg Ser Met Glu Asp Asp Phe Lys Val Val Val
                245                 250                 255

Gly Ile Ser Leu Pro Leu Trp Gly Val Ala Ile Leu Thr Leu Phe Leu
            260                 265                 270

Asp Ile Asn Gly Val Gly Thr Leu Ile Trp Ile Ser Phe Ile Pro Leu
        275                 280                 285

Val Ile Leu Leu Cys Val Gly Thr Lys Leu Glu Met Ile Ile Met Glu
    290                 295                 300

Met Ala Leu Glu Ile Gln Asp Arg Ala Ser Val Ile Lys Gly Ala Pro
305                 310                 315                 320

Val Val Glu Pro Ser Asn Lys Phe Phe Trp Phe His Arg Pro Asp Trp
                325                 330                 335

Val Leu Phe Phe Ile His Leu Thr Leu Phe Gln Asn Ala Phe Gln Met
            340                 345                 350

Ala His Phe Val Trp Thr Val Ala Thr Pro Gly Leu Lys Lys Cys Tyr
        355                 360                 365

His Thr Gln Ile Gly Leu Ser Ile Met Lys Val Val Val Gly Leu Ala
    370                 375                 380

Leu Gln Phe Leu Cys Ser Tyr Met Thr Phe Pro Leu Tyr Ala Leu Val
385                 390                 395                 400

Thr Gln Met Gly Ser Asn Met Lys Arg Ser Ile Phe Asp Glu Gln Thr
                405                 410                 415

Ser Lys Ala Leu Thr Asn Trp Arg Asn Thr Ala Lys Glu Lys Lys Lys
            420                 425                 430

Val Arg Asp Thr Asp Met Leu Met Ala Gln Met Ile Gly Asp Ala Thr
        435                 440                 445

Pro Ser Arg Gly Ser Ser Pro Met Pro Ser Arg Gly Ser Ser Pro Val
    450                 455                 460

His Leu Leu His Lys Gly Met Gly Arg Ser Asp Asp Pro Gln Ser Ala
465                 470                 475                 480

Pro Thr Ser Pro Arg Thr Gln Gln Glu Ala Arg Asp Met Tyr Pro Val
                485                 490                 495

Val Val Ala His Pro Val His Arg Leu Asn Pro Asn Asp Arg Arg Arg
            500                 505                 510

Ser Ala Ser Ser Ser Ala Leu Glu Ala Asp Ile Pro Ser Ala Asp Phe
        515                 520                 525

Ser Phe Ser Gln Gly
    530

<210> SEQ ID NO 40
```

-continued

<211> LENGTH: 542
<212> TYPE: PRT
<213> ORGANISM: Arabidopsis thaliana

<400> SEQUENCE: 40

```
Met Ile Thr Arg Ser Arg Cys Arg Arg Ser Leu Leu Trp Phe Leu Val
  1               5                  10                  15

Phe His Gly Gly Ala Thr Ala Thr Gly Ala Pro Ser Gly Gly Lys Glu
             20                  25                  30

Leu Ser Gln Thr Pro Thr Trp Ala Val Ala Val Val Cys Thr Phe Leu
         35                  40                  45

Ile Leu Ile Ser His Leu Leu Glu Lys Gly Leu Gln Arg Leu Ala Asn
     50                  55                  60

Trp Leu Trp Lys Lys His Lys Asn Ser Leu Leu Glu Ala Leu Glu Lys
 65                  70                  75                  80

Ile Lys Ala Glu Leu Met Ile Leu Gly Phe Ile Ser Leu Leu Leu Thr
                 85                  90                  95

Phe Gly Glu Pro Tyr Ile Leu Lys Ile Cys Val Pro Arg Lys Ala Ala
            100                 105                 110

Leu Ser Met Leu Pro Cys Leu Ser Glu Asp Thr Val Leu Phe Gln Lys
        115                 120                 125

Leu Ala Pro Ser Ser Leu Ser Arg His Leu Leu Ala Ala Gly Asp Thr
    130                 135                 140

Ser Ile Asn Cys Lys Gln Gly Ser Glu Pro Leu Ile Thr Leu Lys Gly
145                 150                 155                 160

Leu His Gln Leu His Ile Leu Leu Phe Phe Leu Ala Ile Phe His Ile
                165                 170                 175

Val Tyr Ser Leu Ile Thr Met Met Leu Ser Arg Leu Lys Ile Arg Gly
            180                 185                 190

Trp Lys Lys Trp Glu Gln Glu Thr Leu Ser Asn Asp Tyr Glu Phe Ser
        195                 200                 205

Ile Asp His Ser Arg Leu Arg Leu Thr His Glu Thr Ser Phe Val Arg
    210                 215                 220

Glu His Thr Ser Phe Trp Thr Thr Thr Pro Phe Phe Phe Tyr Val Gly
225                 230                 235                 240

Cys Phe Phe Arg Gln Phe Phe Val Ser Val Glu Arg Thr Asp Tyr Leu
                245                 250                 255

Thr Leu Arg His Gly Phe Ile Ser Ala His Leu Ala Pro Gly Arg Lys
            260                 265                 270

Phe Asn Phe Gln Arg Tyr Ile Lys Arg Ser Leu Glu Asp Asp Phe Lys
        275                 280                 285

Leu Val Val Gly Ile Ser Pro Val Leu Trp Ala Ser Phe Val Ile Phe
    290                 295                 300

Leu Leu Phe Asn Val Asn Gly Trp Arg Thr Leu Phe Trp Ala Ser Ile
305                 310                 315                 320

Pro Pro Leu Leu Ile Ile Leu Ala Val Gly Thr Lys Leu Gln Ala Ile
                325                 330                 335

Met Ala Thr Met Ala Leu Glu Ile Val Glu Thr His Ala Val Val Gln
            340                 345                 350

Gly Met Pro Leu Val Gln Gly Ser Asp Arg Tyr Phe Trp Phe Asp Cys
        355                 360                 365

Pro Gln Leu Leu Leu His Leu Ile His Phe Ala Leu Phe Gln Asn Ala
    370                 375                 380

Phe Gln Ile Thr His Phe Phe Trp Ile Trp Tyr Ser Phe Gly Leu Lys
```

-continued

```
385                 390                 395                 400

Ser Cys Phe His Lys Asp Phe Asn Leu Val Val Ser Lys Leu Phe Leu
                405                 410                 415

Cys Leu Gly Ala Leu Ile Leu Cys Ser Tyr Ile Thr Leu Pro Leu Tyr
            420                 425                 430

Ala Leu Val Thr Gln Met Gly Ser His Met Lys Lys Ala Val Phe Asp
        435                 440                 445

Glu Gln Met Ala Lys Ala Leu Lys Lys Trp His Lys Asp Ile Lys Leu
    450                 455                 460

Lys Lys Gly Lys Ala Arg Lys Leu Pro Ser Lys Thr Leu Gly Val Ser
465                 470                 475                 480

Glu Ser Phe Ser Leu Ser Ser Ser Ser Ser Ala Thr Thr Leu His Arg
                485                 490                 495

Ser Lys Thr Thr Gly His Ser Ser Asn Ile Ile Tyr Tyr Lys Gln Glu
            500                 505                 510

Asp Glu Glu Asp Glu Met Ser Asp Leu Glu Ala Gly Ala Glu Asp Ala
        515                 520                 525

Ile Asp Arg Ile Gln Gln Gln Glu Met Gln Phe His Asn Ser
    530                 535                 540


<210> SEQ ID NO 41
<211> LENGTH: 526
<212> TYPE: PRT
<213> ORGANISM: Arabidopsis thaliana

<400> SEQUENCE: 41

Met Gly His Gly Gly Glu Gly Met Ser Leu Glu Phe Thr Pro Thr Trp
  1               5                  10                  15

Val Val Ala Gly Val Cys Thr Val Ile Val Ala Ile Ser Leu Ala Val
             20                  25                  30

Glu Arg Leu Leu His Tyr Phe Gly Thr Val Leu Lys Lys Lys Lys Gln
         35                  40                  45

Lys Pro Leu Tyr Glu Ala Leu Gln Lys Val Lys Glu Glu Leu Met Leu
     50                  55                  60

Leu Gly Phe Ile Ser Leu Leu Leu Thr Val Phe Gln Gly Leu Ile Ser
 65                  70                  75                  80

Lys Phe Cys Val Lys Glu Asn Val Leu Met His Met Leu Pro Cys Ser
                 85                  90                  95

Leu Asp Ser Arg Arg Glu Ala Gly Ala Ser Glu His Lys Asn Val Thr
            100                 105                 110

Ala Lys Glu His Phe Gln Thr Phe Leu Pro Ile Val Gly Thr Thr Arg
        115                 120                 125

Arg Leu Leu Ala Glu His Ala Ala Val Gln Val Gly Tyr Cys Ser Glu
    130                 135                 140

Lys Gly Lys Val Pro Leu Leu Ser Leu Glu Ala Leu His His Leu His
145                 150                 155                 160

Ile Phe Ile Phe Val Leu Ala Ile Ser His Val Thr Phe Cys Val Leu
                165                 170                 175

Thr Val Ile Phe Gly Ser Thr Arg Ile His Gln Trp Lys Lys Trp Glu
            180                 185                 190

Asp Ser Ile Ala Asp Glu Lys Phe Asp Pro Glu Thr Ala Leu Arg Lys
        195                 200                 205

Arg Arg Val Thr His Val His Asn His Ala Phe Ile Lys Glu His Phe
    210                 215                 220
```

-continued

Leu Gly Ile Gly Lys Asp Ser Val Ile Leu Gly Trp Thr Gln Ser Phe
225 230 235 240

Leu Lys Gln Phe Tyr Asp Ser Val Thr Lys Ser Asp Tyr Val Thr Leu
245 250 255

Arg Leu Gly Phe Ile Met Thr His Cys Lys Gly Asn Pro Lys Leu Asn
260 265 270

Phe His Lys Tyr Met Met Arg Ala Leu Glu Asp Asp Phe Lys Gln Val
275 280 285

Val Gly Ile Ser Trp Tyr Leu Trp Ile Phe Val Val Ile Phe Leu Leu
290 295 300

Leu Asn Val Asn Gly Trp His Thr Tyr Phe Trp Ile Ala Phe Ile Pro
305 310 315 320

Phe Ala Leu Leu Leu Ala Val Gly Thr Lys Leu Glu His Val Ile Ala
325 330 335

Gln Leu Ala His Glu Val Ala Glu Lys His Val Ala Ile Glu Gly Asp
340 345 350

Leu Val Val Lys Pro Ser Asp Glu His Phe Trp Phe Ser Lys Pro Gln
355 360 365

Ile Val Leu Tyr Leu Ile His Phe Ile Leu Phe Gln Asn Ala Phe Glu
370 375 380

Ile Ala Phe Phe Phe Trp Ile Trp Val Thr Tyr Gly Phe Asp Ser Cys
385 390 395 400

Ile Met Gly Gln Val Arg Tyr Ile Val Pro Arg Leu Val Ile Gly Val
405 410 415

Phe Ile Gln Val Leu Cys Ser Tyr Ser Thr Leu Pro Leu Tyr Ala Ile
420 425 430

Val Ser Gln Met Gly Ser Ser Phe Lys Lys Ala Ile Phe Glu Glu Asn
435 440 445

Val Gln Val Gly Leu Val Gly Trp Ala Gln Lys Val Lys Gln Lys Arg
450 455 460

Asp Leu Lys Ala Ala Ala Ser Asn Gly Asp Glu Gly Ser Ser Gln Ala
465 470 475 480

Gly Pro Gly Pro Asp Ser Gly Ser Gly Ser Ala Pro Ala Ala Gly Pro
485 490 495

Gly Ala Gly Phe Ala Gly Ile Gln Leu Ser Arg Val Thr Arg Asn Asn
500 505 510

Ala Gly Asp Thr Asn Asn Glu Ile Thr Pro Asp His Asn Asn
515 520 525

<210> SEQ ID NO 42
<211> LENGTH: 583
<212> TYPE: PRT
<213> ORGANISM: Arabidopsis thaliana

<400> SEQUENCE: 42

Met Ala Asp Gln Val Lys Glu Lys Thr Leu Glu Glu Thr Ser Thr Trp
1 5 10 15

Ala Val Ala Val Val Cys Phe Val Leu Leu Leu Ile Ser Ile Val Ile
20 25 30

Glu Lys Leu Ile His Lys Ile Gly Ser Trp Phe Lys Lys Lys Asn Lys
35 40 45

Lys Ala Leu Tyr Glu Ala Leu Glu Lys Val Lys Ala Glu Leu Met Leu
50 55 60

Met Gly Phe Ile Ser Leu Leu Leu Thr Ile Gly Gln Gly Tyr Ile Ser
65 70 75 80

-continued

Asn Ile Cys Ile Pro Lys Asn Ile Ala Ala Ser Met His Pro Cys Ser
85 90 95

Ala Ser Glu Glu Ala Arg Lys Tyr Gly Lys Lys Asp Val Pro Lys Glu
100 105 110

Asp Glu Glu Glu Asn Leu Arg Arg Lys Leu Leu Gln Leu Val Asp Ser
115 120 125

Leu Ile Pro Arg Arg Ser Leu Ala Thr Lys Gly Tyr Asp Lys Cys Ala
130 135 140

Glu Lys Gly Lys Val Ala Phe Val Ser Ala Tyr Gly Met His Gln Leu
145 150 155 160

His Ile Phe Ile Phe Val Leu Ala Val Cys His Val Ile Tyr Cys Ile
165 170 175

Val Thr Tyr Ala Leu Gly Lys Thr Lys Met Arg Arg Trp Lys Lys Trp
180 185 190

Glu Glu Glu Thr Lys Thr Ile Glu Tyr Gln Tyr Ser His Asp Pro Glu
195 200 205

Arg Phe Arg Phe Ala Arg Asp Thr Ser Phe Gly Arg Arg His Leu Ser
210 215 220

Phe Trp Ser Lys Ser Thr Ile Thr Leu Trp Ile Val Cys Phe Phe Arg
225 230 235 240

Gln Phe Phe Arg Ser Val Thr Lys Val Asp Tyr Leu Thr Leu Arg His
245 250 255

Gly Phe Ile Met Ala His Leu Ala Pro Gly Ser Asp Ala Arg Phe Asp
260 265 270

Phe Arg Lys Tyr Ile Gln Arg Ser Leu Glu Glu Asp Phe Lys Thr Ile
275 280 285

Val Glu Ile Asn Pro Val Ile Trp Phe Ile Ala Val Leu Phe Leu Leu
290 295 300

Thr Asn Thr Asn Gly Leu Asn Ser Tyr Leu Trp Leu Pro Phe Ile Pro
305 310 315 320

Phe Ile Val Ile Leu Ile Val Gly Thr Lys Leu Gln Val Ile Ile Thr
325 330 335

Lys Leu Gly Leu Arg Ile Gln Glu Lys Gly Asp Val Val Lys Gly Thr
340 345 350

Pro Leu Val Gln Pro Gly Asp His Phe Phe Trp Phe Gly Arg Pro Arg
355 360 365

Phe Ile Leu Phe Leu Ile His Leu Val Leu Phe Thr Asn Ala Phe Gln
370 375 380

Leu Ala Phe Phe Val Trp Ser Thr Tyr Glu Phe Gly Leu Lys Asn Cys
385 390 395 400

Phe His Glu Ser Arg Val Asp Val Ile Ile Arg Ile Ser Ile Gly Leu
405 410 415

Leu Val Gln Ile Leu Cys Ser Tyr Val Thr Leu Pro Leu Tyr Ala Leu
420 425 430

Val Thr Gln Met Gly Ser Lys Met Lys Pro Thr Val Phe Asn Glu Arg
435 440 445

Val Ala Thr Ala Leu Lys Ser Trp His His Thr Ala Lys Lys Asn Ile
450 455 460

Lys His Gly Arg Thr Ser Glu Ser Thr Thr Pro Phe Ser Ser Arg Pro
465 470 475 480

Thr Thr Pro Thr His Gly Ser Ser Pro Ile His Leu Leu Arg Asn Ala
485 490 495

-continued

```
Pro His Lys Arg Ser Arg Ser Val Asp Glu Ser Phe Ala Asn Ser Phe
            500                 505                 510

Ser Pro Arg Asn Ser Asp Phe Asp Ser Trp Asp Pro Glu Ser Gln His
        515                 520                 525

Glu Thr Ala Glu Thr Ser Asn Ser Asn His Arg Ser Arg Phe Gly Glu
    530                 535                 540

Glu Glu Ser Glu Lys Lys Phe Val Ser Ser Ser Val Glu Leu Pro Pro
545                 550                 555                 560

Gly Pro Gly Gln Ile Arg Thr Gln His Glu Ile Ser Thr Ile Ser Leu
                565                 570                 575

Arg Asp Phe Ser Phe Lys Arg
            580
```

PLANT DISEASE RESISTANCE GENES

This case is a divisional of application Ser. No. 09/857,896 filed Jun. 11, 2001, now U.S. Pat. No. 6,846,972 which claimed the benefit of provisional application No. 60/112,737 filed Dec. 18, 1998, the contents of which are hereby incorporated by reference.

FIELD OF THE INVENTION

This invention is in the field of plant molecular biology. More specifically, this invention pertains to nucleic acid fragments encoding disease resistance genes in plants and seeds.

BACKGROUND OF THE INVENTION

It is well established that resistance to many diseases in plants is mediated by the interaction of plant genes referred to as "R" genes with corresponding Avr genes expressed by the pathogen (Hammond-Kosack and Jones (1997) *Ann. Rev. Plant Physiol. Plant Mol. Biol.* 48:1–39). This interaction leads to the activation of plant responses which in turn result in increased resistance to disease. This resistance is frequently mediated by the "hypersensitive response", a localized cell death phenomenon that occurs in the areas of plant tissue invaded by the pathogen. This Avr/R interaction is race-specific; i.e., particular alleles of the plant R gene respond only to specific races of the pathogen which express a corresponding Avr gene (Flor (1971) *Ann. Rev. Phytopathol.* 9:275–296).

Most of the R genes characterized to date are dominant; i.e., resistance is exhibited by plants carrying the appropriate R allele in either a heterozygous or homozygous state. Some R genes have been isolated by map-based cloning. Many homologs of R genes have also been identified by sequence similarity. Because of the rapid evolution of plant resistance to disease, homology of a cDNA or genomic DNA sequence to a known R gene from a different plant species does not allow one to predict the pathogen specificity of that particular R gene. No general methods for such prediction exist today.

Genes involved in resistance of plants to plant pathogens may be used to engineer disease resistance into plants normally sensitive to disease using several different approaches. Transgenic plants containing alleles of R genes demonstrate resistance to corresponding races of the pathogen (Wang et al. (1996) *Mol. Plant-Microbe Interact.* 9:850–855). The resistance genes may also be engineered to respond to non-native signals derived from the pathogen. In addition, pathogen-derived Avr genes may be expressed in a controlled manner in plants to strengthen the response to a pathogen. Genes further downstream from the R genes in the signal transduction pathways that transmit signals to the disease response effector genes may be engineered to directly respond to pathogen infection, thereby shortening the response pathway.

The process of the hypersensitive response to a pathogen, and the signaling networks involved, are poorly understood. In no case have all of the genes involved in transmitting the signal from the pathogen to the site of the initiation of the hypersensitive response been identified.

In a few cases, the functioning of a disease resistance mechanism different from the Avr/R interaction described above results in a recessive, rather than dominant pattern of resistance. One such example is the Mlo gene of barley, which conveys resistance to *Erysiphe graminis f.* sp. *hordei*.

The barley gene has been recently isolated by a positional cloning approach (Bueschges et, al. (1997) *Cell* 88:695–705). The dominant (sensitive) allele (Mlo) is thought to encode a protein involved in regulation of leaf cell death, and in the onset of pathogen defense. The partial or complete inactivation of Mlo results in the priming of the disease-resistance response even in the absence of the pathogen, and leads to increased resistance to *E. graminis.*

The available scientific data concerning Mlo-mediated, disease resistance in barley points towards another approach to controlling disease priming the pathogen response pathway by diminishing the effectiveness of negative regulation of the hypersensitive response. Appropriately engineered plants may show increased pathogen, resistance at the expense of expressing some pathogen response related genes even in the absence of pathogen. Sense or antisense inhibition or targeted gene disruption of Mlo and Mlo-related genes may have such an effect. Resistance to other pathogens may also be increased using this approach.

Mlo-related cDNA clones and DNA segments of genomic DNA, and their homologs and derivatives, may also be used as molecular probes to track inheritance of corresponding loci in genetic crosses, and thus facilitate the plant breeding process. Moreover, these DNA sequences may also be used as probes to isolate, identify and genetically map Mlo and other closely related disease resistance genes.

SUMMARY OF THE INVENTION

The present invention relates to isolated polynucleotides comprising a nucleotide sequence encoding a polypeptide of at least 66 amino acids that has at least 95% identity based on the Clustal method of alignment when compared to a polypeptide selected from the group consisting of an Mlo homolog polypeptide of SEQ ID NOs:2, 4, 6, 8, 10, 12, 14, 16, 18, 20, 22, 24, 26, 28, 30, 32, 34, 36, and 38. The present invention also relates to an isolated polynucleotide comprising the complement of the nucleotide sequences described above.

It is preferred that the isolated polynucleotide of the claimed invention consists of a nucleic acid sequence selected from the group consisting of SEQ ID NOs:1, 3, 5, 7, 9, 11, 13, 15, 17, 19, 21, 23, 25, 27, 29, 31, 33, 35, and 37 that codes for the polypeptide selected from the group consisting of SEQ ID NOs:2, 4, 6, 8, 10, 12, 14, 16, 18, 20, 22, 24, 26, 28, 30, 32, 34, 36, and 38. The present invention also relates to an isolated polynucleotide comprising a nucleotide sequences of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, and 37 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention the process comprising either transforming or transfecting an isolated compatible host cell with a chimeric gene or isolated polynucleotide of the present invention.

The present invention relates to an Mlo homolog polypeptide of at least 66 amino acids comprising at least 95% homology based on the Clustal method of alignment compared to a polypeptide selected from the group consisting of SEQ ID NOs:2, 4, 6, 8, 10, 12, 14, 16, 18, 20, 22, 24, 26, 28, 30, 32, 34, 36, and 38.

The present invention relates to a method of selecting an isolated polynucleotide that affects the level of expression of an Mlo homolog polypeptide in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level an Mlo homolog polypeptide in the host cell containing the isolated polynucleotide; and (d) comparing the level of an Mlo homolog polypeptide in the host cell containing the isolated polynucleotide with the level of an Mlo homolog polypeptide in the host cell that does not contain the isolated polynucleotide.

The present invention relates to a method of obtaining a nucleic acid fragment encoding a substantial portion of an Mlo homolog polypeptide gene, preferably a plant Mlo homolog polypeptide gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, and 37 and the complement of such nucleotide sequences; and amplifying a nucleic acid fragment (preferably a cDNA inserted in a cloning vector) using the oligonucleotide primer. The amplified nucleic acid fragment preferably will encode a portion of an Mlo homolog amino acid sequence.

The present invention also relates to a method of obtaining a nucleic acid fragment encoding all or a substantial portion of the amino acid sequence encoding an Mlo homolog polypeptide comprising the steps of: probing a cDNA or genomic library with an isolated polynucleotide of the present invention: identifying a DNA clone that hybridizes with an isolated polynucleotide of the present invention: isolating the identified DNA clone; and sequencing the cDNA or genomic fragment that comprises the isolated DNA clone.

The present invention relates to a composition, such as a hybridization mixture, comprising an isolated polynucleotide of the present invention.

The present invention relates to an isolated polynucleotide of the present invention comprising at least one of 35 contiguous nucleotides derived from a nucleic acid sequence selected from the group consisting of SEQ ID NOs:1, 3, 5, 7, 9, 11, 13, 15, 17, 19, 21, 23, 25, 27, 29, 31, 33, 35, and 37.

The present invention relates to an expression cassette comprising an isolated polynucleotide of the present invention operably linked to a promoter.

The present invention relates to a method for positive selection of a transformed cell comprising: (a) transforming a host cell with the chimeric gene of the present invention or an expression cassette of the present invention; and (b) growing the transformed host cell, preferably plant cell, such as a monocot or a dicot, under conditions which allow expression of the Mlo homolog polynucleotide in an amount sufficient to complement a null mutant to provide a positive selection means.

BRIEF DESCRIPTION OF THE DRAWING AND SEQUENCE DESCRIPTIONS

The invention can be more fully understood from the following detailed description and the accompanying drawing and Sequence Listing which form a part of this application.

FIGS. 1A–1F show a comparison of the amino acid sequences of the Mlo homolog from soybean clone sdp4c.pk003.111 (SEQ ID NO:08), soybean clone sr1.pk0049.c5 (SEQ ID NO:12), soybean clone src2c.pk002.h11 (SEQ ID NO:14), soybean clone sdp2c.pk026.g24:fis (SEQ ID NO:28), wheat clone wdr1.pk0006.a3:cgs (SEQ ID NO:32), whet clone wlmk4.pk0025.f7:fis (SEQ ID NO:38), *Hordeum vulgare* having NCBI General Identifier No. 1877221 (SEQ ID NO:39), *Arabidopsis thaliana* having NCBI General Identifier No. 2494143 (SEQ ID NO:40), *Arabidopsis thaliana* having NCBI General Identifier No. 2765817 (SEQ ID NO:41), and *Arabidopsis thaliana* having NCBI General Identifier No. 4585879 (SEQ ID NO:42). Dashes are used by the program to maximize the alignment of the sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Disease Resistance Genes

| Protein | Clone Designation | SEQ ID NO: (Nucleotide) | SEQ ID NO: (Amino Acid) |
|---|---|---|---|
| Rice Mlo Homolog | Contig of:<br>rl0n.pk105.g24<br>rls24.pk0009.g5 | 1 | 2 |
| Rice Mlo Homolog | rlr24.pk0047.b5 | 3 | 4 |
| Rice Mlo Homolog | rr1.pk078.d1 | 5 | 6 |
| Soybean Mlo Homolog | sdp4c.pk003.l11 | 7 | 8 |
| Soybean Mlo Homolog | sds9n.pk001.j10 | 9 | 10 |
| Soybean Mlo Homolog | sr1.pk0049.c5 | 11 | 12 |
| Soybean Mlo Homolog | src2c.pk002.h11 | 13 | 14 |
| Wheat Mlo Homolog | wdr1.pk0006.a3 | 15 | 16 |
| Wheat Mlo Homolog | wlmk4.pk0025.f7 | 17 | 18 |
| Wheat Mlo Homolog | wre1n.pk0154.g11 | 19 | 20 |
| Rice Mlo Homolog | rl0n.pk087.m5 | 21 | 22 |
| Rice Mlo Homolog | Contig of:<br>rl0n.pk128.i12<br>rth1c.pk006.o23.f | 23 | 24 |
| Rice Mlo Homolog | rtc1c.pk001.c23.f | 25 | 26 |
| Soybean Mlo Homolog | sdp2c.pk026.g24 | 27 | 28 |
| Soybean Mlo Homolog | sfl1.pk0104.g10 | 29 | 30 |
| Wheat Mlo Homolog | wdr1.pk0006.a3:cgs | 31 | 32 |
| Wheat Mlo Homolog | wlm0.pk039.m9 | 33 | 34 |
| Wheat Mlo Homolog | wlm96.pk046.j8 | 35 | 36 |
| Wheat Mlo Homolog | wlmk4.pk0025.f7:fis | 37 | 38 |

The Sequence Listing contains the one letter code for nucleotide sequence characters and the three letter codes for amino acids as defined in conformity with the IUPAC- IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOs:1, 3, 5, 7, 9, 11, 13, 15, 17, 19, 21, 23, 25, 27, 29, 31, 33, 35, 37, or the complement of such sequences.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-á-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, or the complement of such nucleotide sequences may be used in methods of selecting an isolated polynucleotide that affects the expression of a polypeptide (an Mlo homolog) in a host cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least about 50 amino acids, preferably at least about 100 amino acids, more preferably at least about 150 amino acids, still more preferably at least about 200 amino acids, and most preferably at least about 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pair wise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410;). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers, to a nucleotide sequence that codes for a specific amino acid sequence. "Regulatory, sequences" refer to nucleotide sequences located upstream (5' non-coding sequences), within or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered: numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence. i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expressions", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulun, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (*London*) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual;* Cold Spring Harbor Laboratory Press: Cold Spring Harbor, 1989 (hereinafter "Maniatis").

Nucleic acid fragments encoding at least a portion of several Mlo homologs have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other Mlo homologs, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, and 37 and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as Mlo homologs) preferably a substantial portion of a plant polypeptide of a gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, and 37, and the complement of such nucleotide sequences; and amplifying a nucleic acid fragment (preferably a cDNA inserted in a cloning vector) using the oligonucleotide primer. The amplified nucleic acid fragment preferably will encode a portion of an Mlo homolog polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of disease resistance in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or compressions (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of fore proteins are well known to those skilled in the art. Any of these could be used to construct a chimeric gene for production of the instant polypeptides. This chimeric gene could then be introduced into appropriate microorganisms via transformation to provide high level expression of the encoded Mlo homolog. An example of a vector for high level expression of the instant polypeptides in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various chances and modifications of the invention to adapt it to various usages and conditions.

Example 1

Composition of cDNA Libraries; Isolation and Sequencing of cDNA Clones cDNA libraries representing mRNAs from various rice, soybean, and wheat tissues were prepared. The characteristics of the libraries are described below.

TABLE 2 cDNA Libraries from Rice, Soybean, and Wheat

| Library | Tissue | Clone |
|---|---|---|
| rl0n | Rice 15 Day Old Leaf* | rl0n.pk087.m5 |
| rl0n | Rice 15 Day Old Leaf* | rl0n.pk105.g24 |
| rl0n | Rice 15 Day Old Leaf* | rl0n.pk128.i12 |
| rlr24 | Rice Leaf 15 Days After Germination. 24 Hours After Infection of Strain *Magaporthe grisea* 4360-R-62 (AVR2-YAMO); Resistant | rlr24.pk0047.b5 |
| rls24 | Rice Leaf 15 Days After Germination, 24 Hours After Infection of Strain *Magaporthe grisea* 4360-R-67 (AVR2-YAMO); Susceptible | rls24.pk0009.g5 |
| rr1 | Rice Root of Two Week Old Developing Seedling | rr1.pk078.d1 |
| rtc1c | Rice Leaf Harvested 4, 8, and 24 Hours After Inoculation With Fungal Strain 0184, Pooled. | rtc1c.pk001.c23.f |
| rth1c | Rice Leaf Inoculated With Fungal Strain 429 | rth1c.pk006.o23.f |
| sdp2c | Soybean Developing Pods (6–7 mm) | sdp2c.pk026.g24 |
| sdp4c | Soybean Developing Pods (10–12 mm) | sdp4c.pk003.l11 |
| sds9n | Soybean Developing Seeds 6 to 26 Days After Flowering* | sds9n.pk001.j10 |
| sfl1 | Soybean Immature Flower | sfl1.pk0104.g10 |
| sr1 | Soybean Root | sr1.pk0049.c5 |
| sr1 | Soybean Root | src2c.pk002.h11 |
| wdr1 | Wheat Developing Root and Leaf | wdr1.pk0006.a3 |
| wlm0 | Wheat Seedlings 0 Hour After Inoculation With *Erysiphe graminis f.* sp *tritici* | wlm0.pk039.m9 |
| wlm96 | Wheat Seedlings 96 Hours After Inoculation With *Erysiphe graminis f.* sp *tritici* | wlm96.pk046.j8 |
| wlmk4 | Wheat Seedlings 4 Hours After Inoculation With *Erysiphe graminis f.* sp *tritici* and treatment with Herbicide** | wlmk4.pk0025.f7 |
| wre1n | Wheat Root From 7 Day Old Etiolated Seedling* | wre1n.pk0154.g11 |

*These libraries were normalized essentially as described in U.S. Pat. No. 5,482,845, incorporated herein by reference.
**Application of 6-iodo-2-propoxy-3-propyl-4(3H)-quinazolinone: synthesis and methods of using this compound are described in USSN 08/545.827, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding Mlo homologs were identified by conducting BLAST (Basic Local Alignment Search Tool; Altschul et al. (1993) *J. Mol. Biol.* 215:403–410; searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value the greater the likelihood that the cDNA sequence and the BLAST "hit" represent homologous proteins.

Example 3

Characterization of cDNA Clones Encoding Mlo Homologs

The BLASTX search using the nucleotide sequences from clones listed in Table 3 revealed similarity of the polypeptides encoded by the cDNAs to Mlo protein from *Hordeum vulgare* (NCBI General Identifier No. 1877221), by the BAC genomic sequences to Mlo homologs from *Arabidopsis thaliana* (NCBI General Identifier Nos. 2459447, 3212880), or by the contig to Mlo-hl from *Arabidopsis thaliana* (NCBI General Identifier No. 2765817). Shown in Table 3 are the BLAST results for individual ESTs ("EST"), the sequences of the entire cDNA inserts comprising the indicated cDNA clones ("FIS"), contigs assembled from an FIS and one or more ESTs ("Contig*"), or sequences encoding the entire protein derived from an FIS, or an FIS and PCR ("CGS").

TABLE 3

BLAST Results for Sequences Encoding Polypeptides Homologous to Mlo Protein

| Clone | Status | NCBI General Identifier No. | BLAST pLog Score |
|---|---|---|---|
| Contig of: rl0n.pk105.g24 rls24.pk0009.g5:fis | Contig* | 2459447 | 60.00 |
| rlr24.pk0047.b5 | EST | 3212880 | 9.70 |
| rr1.pk078.d1 | EST | 1877221 | 42.70 |
| sdp4c.pk003.l11 | FIS | 2765817 | <254 |
| sds9n.pk001.j10 | EST | 1877221 | 117.0 |
| sr1.pk0049.c5 | FIS | 2494143 | 167.0 |
| src2c.pk002.h11 | FIS | 2765817 | 36.04 |
| wdr1.pk0006.a3 | FIS | 1877221 | 116.0 |
| wlmk4.pk0025.f7 | EST | 2765817 | 166.0 |
| wre1n.pk0154.g11 | EST | 2765817 | 21.00 |

The sequence from the contig assembled from clones rl0n.pk105.g24 and rls24.pk0009.g5:fis and shown in SEQ ID NO:1, is identical to the sequence of the entire cDNA insert in clone rl0n.pk105.g24, and contains two introns. The first intron encompasses nucleotides 379 through 680 and the second intron contains nucleotides 716 through 800. The sequence of the entire cDNA insert in clone wlmk4.pk0025.f7 was determined, PCR was used to determine the 5' sequence from clone wdrl.pk0006.a3, and further sequencing and searching of the DuPont proprietary database allowed the identification of other clones encoding Mlo homologs. The BLASTX search using the nucleotide sequences from clones listed in Table 4 revealed similarity of the polypeptides encoded by the cDNAs to Mlo protein from *Hordeum vulgare* (NCBI General Identifier No. 1877221), by the contigs to Mlo homologs from *Arabidopsis thaliana* (NCBI General Identifier Nos. 5051767 and 4585879), by the contig to Mlo-hl from *Hordeum vulgare* (NCBI General Identifier No. 2765821), or by the contig to Mlo-hl homolog from *Arabidopsis thaliana* (NCBI General Identifier No. 2765817). Shown in Table 4 are the BLAST results for individual ESTs ("EST"), the sequences of the entire cDNA inserts comprising the indicated cDNA clones ("FIS"), contigs assembled from two or more ESTs ("Contig"), or sequences encoding the entire protein derived from an FIS, or an FIS and PCR ("CGS"):

TABLE 4

BLAST Results for Sequences Encoding Polypeptides Homologous to Mlo Protein

| Clone | Status | NCBI General Identifier No. | BLAST pLog Score |
|---|---|---|---|
| rl0n.pk087.m5 | EST | 2765817 | 78.00 |
| Contig of: rl0n.pk128.i12 rth1c.pk006.o23.f | Contig | 2765817 | 55.70 |
| rtc1c.pk001.c23.f | EST | 5051767 | 22.30 |
| sdp2c.pk026.g24 | FIS | 4585879 | 107.00 |
| sfl1.pk0104.g10 | EST | 4585879 | 27.00 |
| wdr1.pk0006.a3:cgs | CGS | 1877221 | >254.00 |
| wlm0.pk039.m9 | EST | 2765821 | 23.52 |

TABLE 4-continued

BLAST Results for Sequences Encoding Polypeptides Homologous to Mlo Protein

| Clone | Status | NCBI General Identifier No. | BLAST pLog Score |
|---|---|---|---|
| wlm96.pk046.j8 | EST | 5051767 | 41.30 |
| wlmk4.pk0025.f7:fis | CGS | 2765817 | 150.00 |

FIGS. 1A–1F presents an alignment of the amino acid sequences set forth in SEQ ID NOs:8, 12, 14, 28, 32, and 38, the *Hordeum vulgare* Mlo sequence (SEQ ID. NO:39), the *Arabidopsis thaliana* Mlo homolog sequences (SEQ ID NO:40 and SEQ ID NO:42), and the *Arabidopsis thaliana* Mlo-hl sequence (SEQ ID NO:41). The data in Table 5 presents a calculation of the percent identity of the amino acid sequences set forth in SEQ ID NOs:2, 4, 6, 8, 10, 12, 14, 16, 18, 20, 22, 24, 26, 28, 30, 32, 34, 36, and 38 and the *Hordeum vulgare* Mlo sequence (SEQ ID NO:39), the *Arabidopsis thaliana* Mlo homolog sequences (SEQ ID NO:40 and SEQ ID NO:42), and the *Arabidopsis thaliana* Mlo-hl sequence (SEQ ID NO:41).

TABLE 4

Percent Identity of Amino Acid Sequences Deduced From the Nucleotide Sequences of cDNA Clones Encoding Polypeptides Homologous to Mlo Protein

| | Percent Identity to | | | |
|---|---|---|---|---|
| SEQ ID NO. | 1877221 | 2494143 | 2765817 | 4585879 |
| 2 | 32.3 | 38.1 | 31.3 | 31.6 |
| 4 | 22.9 | 31.2 | 27.5 | 25.7 |
| 6 | 58.5 | 18.5 | 14.6 | 22.3 |
| 8 | 35.9 | 36.7 | 65.9 | 36.5 |
| 10 | 92.0 | 36.9 | 31.0 | 40.1 |
| 12 | 39.7 | 53.3 | 36.3 | 40.5 |
| 14 | 39.4 | 45.2 | 63.5 | 48.1 |
| 16 | 92.8 | 32.0 | 26.6 | 35.6 |
| 18 | 37.6 | 36.7 | 54.9 | 38.0 |
| 20 | 19.7 | 18.5 | 31.8 | 23.6 |
| 22 | 36.7 | 41.4 | 65.1 | 37.9 |
| 24 | 28.0 | 25.6 | 38.6 | 28.5 |
| 26 | 31.5 | 29.7 | 39.6 | 36.0 |
| 28 | 45.6 | 45.6 | 38.0 | 63.8 |
| 30 | 44.2 | 33.8 | 27.3 | 63.6 |
| 32 | 86.9 | 41.1 | 34.8 | 43.9 |
| 34 | 51.5 | 43.9 | 36.4 | 39.4 |
| 36 | 44.1 | 39.4 | 46.5 | 39.4 |
| 38 | 35.5 | 34.1 | 51.9 | 35.5 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10. GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode substantial portions of rice, soybean, and wheat Mlo homologs and entire or nearly entire soybean and wheat Mlo homologs. These sequences represent the first rice, soybean, and wheat sequences encoding Mlo homologs.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit, U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of 4 *Agrobacterium tumefaciens.*

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco 1 (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli;* Gritz et al.(1983) *Gene* 25:179–188) and the 3' region of the nopaline synthase gene from the T-DNA of the Ti plasmid of *Agrobacterium tumefaciens.* The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1μg/μL), 20 μl spermidine (0.1 M), and 50 μL $CaCl_2$ (2.5 M). The particle preparation is then agitated for three minutes, spun in a microbe for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransferred, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropolthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

What is claimed is:

1. An isolated polynuoleotide comprising:

a) a nucleotide sequence encoding a polypeptide of an Mlo protein, wherein said polypeptide has an amino acid sequence of at least 90% sequence identity, based on the Clustal method of alignment, when compared to a polypeptide of SEQ ID NO:12 and further wherein said polypeptide has disease resistance activity against *Erysiphe graminals* when expressed in a plant; or b) a complement of the nucleotide sequence, wherein the complement and the nucleotide sequence have the same number of nuoleotides and are 100% complementary.

2. The polynucleotide of claim 1 wherein the sequence identity is at least 95%.

3. The polynucleotide of claim 1 wherein the amino acid sequence of the polypeptide comprises SEQ ID NO:12.

4. The polynucleotide of claim 1 wherein the polynucleotide comprises SEQ ID NO:11.

5. A recombinant DNA construct comprising all or a part of the polynucleotide of claim 1 operably linked to at least one regulatory sequence.

6. A host cell comprising the recombinant DNA construct of claim 5.

7. The cell of claim 6, wherein the cell is selected from the group consisting of a yeast cell, a bacterial cell, an insect cell, and a plant cell.

8. A transgenic plant comprising the recombinant DNA construct of claim 5.

9. A method for transforming a cell comprising introducing into a cell the recombinant DNA construct of claim 5.

10. A method for producing a transgenic plant comprising (a) transforming a plant cell with the recombinant DNA construct of claim 5, and (b) regenerating a transgenic plant from the transformed plant cell.

11. The recombinant DNA construct of claim 5, wherein the recombinant DNA construct is an expression vector.

* * * * *